United States Patent
Hagemann et al.

(12) 
(10) Patent No.: US 6,288,102 B1
(45) Date of Patent: Sep. 11, 2001

(54) SUBSTITUTED PHENYLKETOENOLS AND THEIR USE AS PESTICIDES AND HERBICIDES

(75) Inventors: Hermann Hagemann, Leverkusen; Reiner Fischer, Monheim; Thomas Bretschneider, Lohmar; Christoph Erdelen, Leichlingen; Ulrike Wachendorff-Neumann, Neuwied; Peter Dahmen, Neuss, all of (DE); Markus Dollinger, Overland Park, KS (US); Alan Graff, Köln; Wolfram Andersch, Bergisch Gladbach, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/319,489

(22) PCT Filed: Dec. 1, 1997

(86) PCT No.: PCT/EP97/06708

§ 371 Date: Jun. 4, 1999

§ 102(e) Date: Jun. 4, 1999

(87) PCT Pub. No.: WO98/25928

PCT Pub. Date: Jun. 18, 1998

(30) Foreign Application Priority Data

Dec. 12, 1996 (DE) .................................. 196 51 686

(51) Int. Cl.⁷ .................. A61K 31/407; A01N 45/02; C07D 491/107

(52) U.S. Cl. .................. 514/409; 548/410; 504/116.1; D22/120

(58) Field of Search ............... 514/409; 548/410; 504/116.1; D22/120

(56) References Cited

U.S. PATENT DOCUMENTS

| | | | |
|---|---|---|---|
| 5,258,527 | 11/1993 | Krauskopf et al. | 456/543 |
| 5,262,383 | 11/1993 | Fischer et al. | 528/195 |
| 5,462,913 | 10/1995 | Fischer et al. | 596/138 |
| 5,504,057 | 4/1996 | Fischer et al. | 613/283 |
| 5,567,671 | 10/1996 | Fischer | 613/283 |
| 5,602,078 | 2/1997 | Fischer | 613/283 |
| 5,622,917 | 4/1997 | Fischer et al. | 668/283 |
| 5,677,449 | 10/1997 | Fischer et al. | 596/165 |
| 5,830,825 | 11/1998 | Fischer et al. | 96/130 |
| 5,945,444 | 8/1999 | Fischer et al. | 95/445 |

FOREIGN PATENT DOCUMENTS

95/26954 * 10/1995 (WO) .

* cited by examiner

Primary Examiner—T. A. Solola
(74) Attorney, Agent, or Firm—Joseph C. Gil; James R. Franks; Jackie Ann Zurcher

(57) ABSTRACT

The invention relates to novel phenyl-substituted cyclic ketoenols of the formula (I)

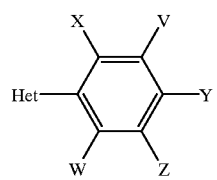

(I)

in which

Het represents one of the groups

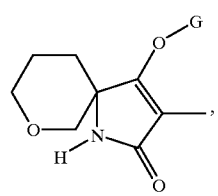

(1)

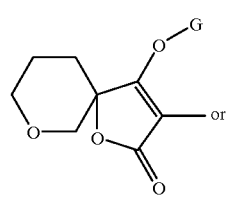

(2)

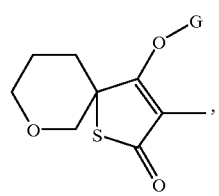

(3)

and G, V, W, X, Y and Z are each as defined in the description, to processes and intermediates for their preparation and to their use as pesticides and herbicides.

8 Claims, No Drawings

SUBSTITUTED PHENYLKETOENOLS AND THEIR USE AS PESTICIDES AND HERBICIDES

This application is a 371 of PCT/EP97/06708 filed Dec. 1, 1997.

TECHNICAL FIELD OF THE INVENTION

The invention relates to novel phenyl-substituted cyclic ketoenols, to a plurality of processes and intermediates for their preparation and to their use as pesticides and herbicides.

BACKGROUND OF THE INVENTION

It is already known that certain phenyl-substituted cyclic ketoenols are active as insecticides, acaricides and/or herbicides.

1H-arylpyrrolidine-dione derivatives (EP-A-456 063, EP-A-521 334, EP-A-596 298, EP-A-613 884, EP-A-613 885, DE 44 40 594, WO 94/01 997, WO 95/01 358, WO 95/20 572, EP-A-668 267, WO 95/26 954, WO 96/25395 and WO 96/35 664) having insecticidal, acaricidal and in some cases herbicidal activity are known.

It is known that certain substituted $\Delta^3$-dihydrofuran-2-one-derivatives have herbicidal properties (cf. DE-A-4 014 420). The synthesis of the tetronic acid derivatives (such as, for example, 3-(2-methyl-phenyl)-4-hydroxy-5-(4-fluorophenyl)-$\Delta^3$-dihydrofuran-(2)-one) used as starting materials is also described in DE-A-4 014 420. Compounds of a similar structure are known from the publication Campbell et al., J. Chem. Soc., Perkin Trans. 1, 1985, (8) 1567–76, without an insecticidal and/or acaricidal activity being mentioned. Furthermore, 3-aryl-$\Delta^3$-dihydrofuranone derivatives having herbicidal, acaricidal and insecticidal properties are known from EP-A-528 156, EP-A-0 647 637, WO 96/25395, WO 96/20196 and the abovementioned hitherto undisclosed patent application. 3-aryl-$\Delta^3$-dihydrothiophene-one derivatives are also known (WO 95/26 345, WO 96/25395 and WO 96/35664).

However, the acaricidal and insecticidal activity and/or spectrum of activity and/or plant tolerance of these compounds, in particular with respect to crop plants, is not always satisfactory.

DETAILED DESCRIPTION OF THE INVENTION

The invention, accordingly, provides novel compounds of the formula (I)

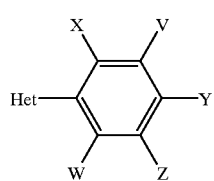

(I)

in which
V represents hydrogen, halogen, alkyl or alkoxy,
W represents hydrogen, cyano, nitro, halogen, alkyl, alkenyl, alkinyl, alkoxy, halogenoalkyl, halogenoalkoxy or in each case optionally substituted phenyl, phenoxy, phenylthio, phenylalkoxy or phenylalkylthio,
X represents halogen, alkyl, alkenyl, alkinyl, alkoxy, halogenoalkyl, halogenoalkoxy, cyano, nitro or in each case optionally substituted phenyl, phenoxy, phenylthio, phenylalkyloxy or phenylalkylthio,
Y represents hydrogen, halogen, alkyl, alkoxy, halogenoalkyl, halogenoalkoxy, cyano or nitro,
Z represents hydrogen, halogen, alkyl, alkoxy, halogenoalkyl, halogenoalkoxy, hydroxyl, cyano, nitro or in each case optionally substituted phenoxy, phenylthio, 5- or 6-membered hetaryloxy, 5- or 6-membered hetarylthio, phenylalkyloxy or phenylalkylthio, or
Y and Z together with the linking carbon atoms represent an optionally substituted cycle which is optionally interrupted by one or more heteroatoms, or
W and Z together with the linking carbon atoms represent an optionally substituted cycle which is optionally interrupted by one or more heteroatoms,
Het represents one of the groups

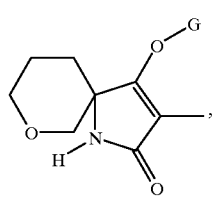

(1)

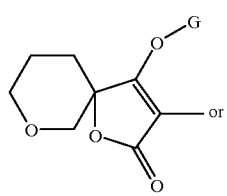

(2)

or

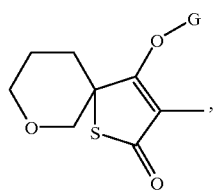

(3)

in which
G represents hydrogen (a) or represents one of the groups

(b)

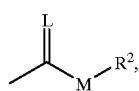

(c)

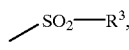

(d)

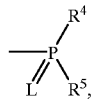

(e)

-continued

E, or

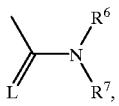
(f)

(g)

in which
E represents a metal ion equivalent or an ammonium ion,
L represents oxygen or sulphur,
M represents oxygen or sulphur, $R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, $R^2$ represents in each case optionally halogen- or cyano-substituted alkyl, alkenyl, alkoxyalkyl or polyalkoxyalkyl or represents in each case optionally substituted cycloalkyl, phenyl or benzyl, $R^3$, $R^4$ and $R^5$ independently of one another each represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, $R^6$ and $R^7$ independently of one another each represent hydrogen, represent in each case optionally halogen- or cyano-substituted alkyl, cycloalkyl, alkenyl, alkoxy, alkoxyalkyl or represent in each case optionally substituted phenyl or benzyl, or together with the linking N atom form an optionally oxygen- or sulphur-containing and optionally substituted cycle.

The compounds of the formula (I) can be present, depending, inter alia, on the nature of the substituents, as optical isomers or isomer mixtures of differing composition which, if appropriate, can be separated in a customary manner. Both the pure isomers and the isomer mixtures, their preparation and use, and compositions comprising them are part of the subject matter of the present invention. In the following, for simplicity, however, compounds of the formula (I) are always referred to, although pure compounds and, if appropriate, mixtures having different proportions of isomeric compounds are intended.

Including the meanings (1) to (3) of the group Het, the following principal structures (I-1) to (I-3) result:

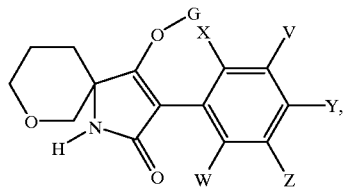
(I-1)

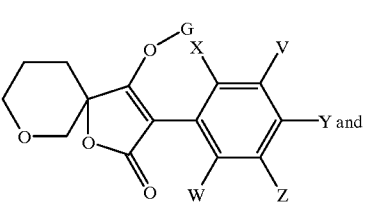
(I-2)

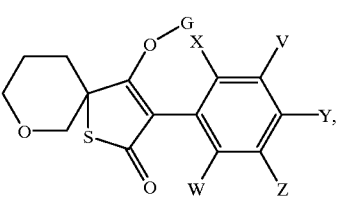
(I-3)

in which
G, V, W, X, Y and Z are each as defined above.

Including the various meanings (a), (b), (c), (d), (e), (f) and (g) of the group G, the following principal structures (I-1-a) to (I-1-g) result if Het represents the group (1)

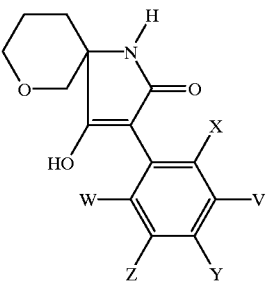
(I-1-a)

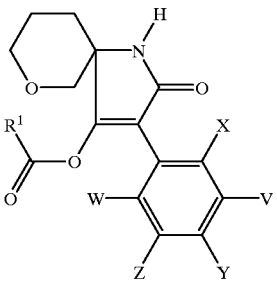
(I-1-b)

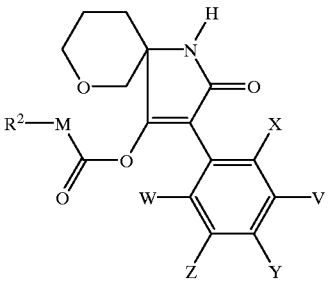
(I-1-c)

(I-1-d)
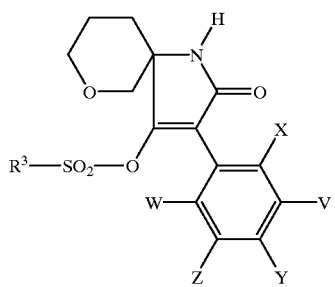
(I-1-e)
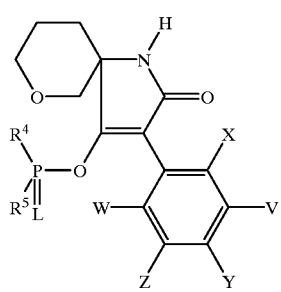
(I-1-f)
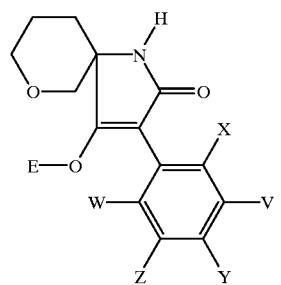
(I-1-g)
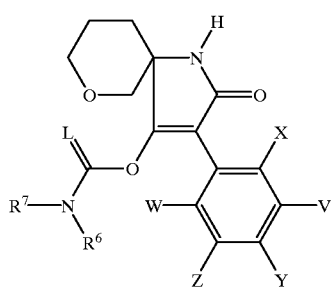
in which
E, L, M, V, W, X, Y, Z, $R^1$, $R^2$, $R^3$, $R^4$, $R^5$, $R^6$ and $R^7$ are each as defined above.
Including the various meanings (a), (b), (c), (d), (e), (f) and (g) of the group G, the following principal structures (I-2-a) to (I-2-g) result if Het represents the group (2)
(I-2-a)
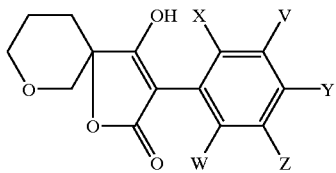
(I-2-b)
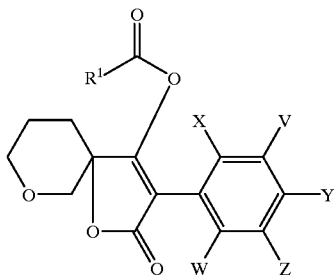
(I-2-c)
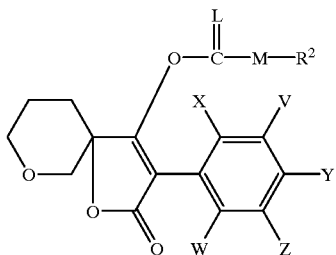
(I-2-d)
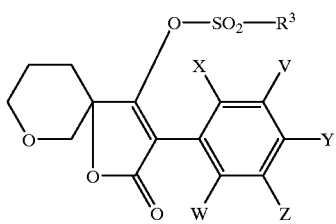
(I-2-e)
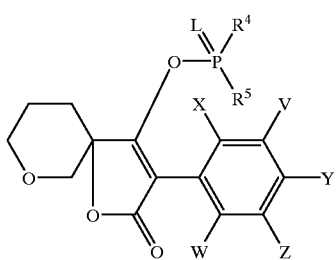
(I-2-f)
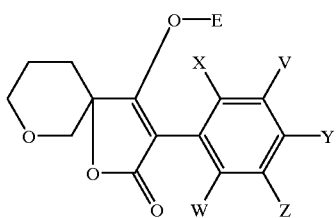

(I-2-g)

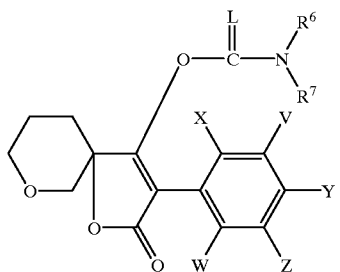

in which

E, L, M, V, W, X, Y, Z, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-3-a) to (I-3-g) result if Het represents the group (3)

(I-3-a)

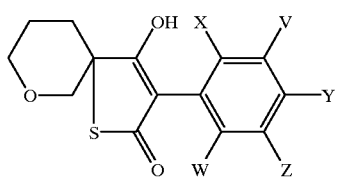

(I-3-b)

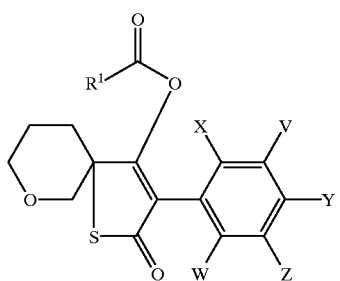

(I-3-c)

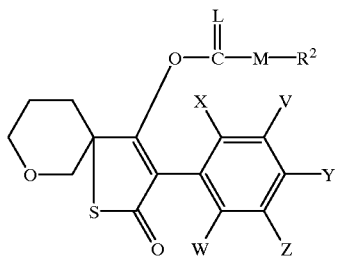

(I-3-d)

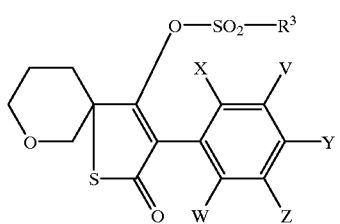

(I-3-e)

(I-3-f)

(I-3-g)

in which

E, L, M, V, W, X, Y, Z, $R^1$, $R^2$, $R^3$, $R^4$, $R^5$, $R^6$ and $R^7$ are each as defined above.

Furthermore, it has been found that the novel compounds of the formula (I) are obtained by the processes described below:

(A) compounds of the formula (I-1-a)

(I-1-a)

in which

V, W, X, Y and Z are as defined above are obtained when compounds of the formula (II)

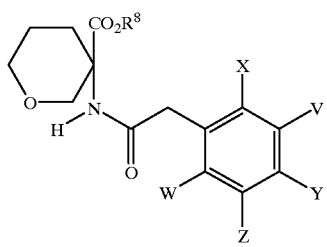

(II)

in which
V, W, X, Y and Z are each as defined above
and
$R^8$ represents alkyl (preferably $C_1$–$C_6$-alkyl)
are intramolecularly condensed in the presence of a diluent and in the presence of a base.
(B) Moreover, it has been found that compounds of the formula (I-2-a)

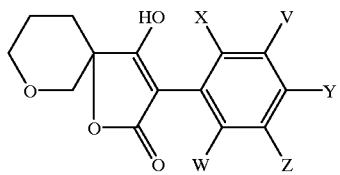

(I-2-a)

in which
V, W, X, Y and Z are each as defined above
are obtained when
compounds of the formula (III)

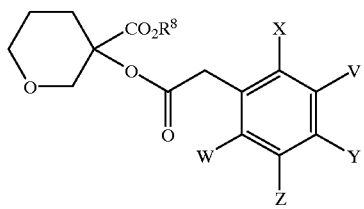

(III)

in which
V, W, X, Y, Z and $R^8$ are each as defined above
are intramolecularly condensed in the presence of a diluent and in the presence of a base.
(C) Furthermore, it has been found that compounds of the formula (I-3-a)

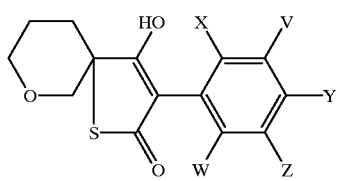

(I-3-a)

in which
V, W, X, Y and Z are each as defined above
are obtained when
compounds of the formula (IV)

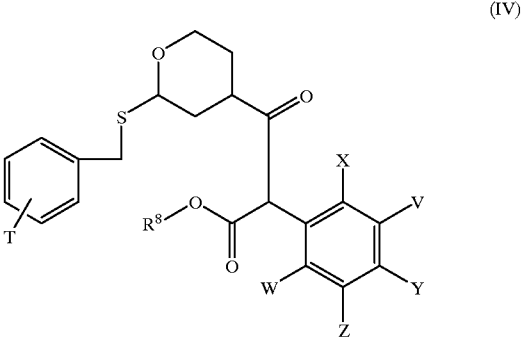

(IV)

in which
V, W, X, Y, Z and $R^8$ are each as defined above and
T represents hydrogen, halogen, alkyl (preferably $C_1$–$C_6$-alkyl) or alkoxy (preferably $C_1$–$C_8$-alkoxy)
are intramolecularly cyclized, if appropriate in the presence of a diluent and in the presence of an acid.
Moreover, it has been found
(D) that the compounds of the formulae (I-1-b) to (I-3-b) shown above in which $R^1$, V, W, X, Y and Z are each as defined above are obtained when compounds of the formulae (I-1-a) to (I-3-a) shown above in which V, W, X, Y and Z are each as defined above are in each case reacted
α) with acyl halides of the formula (V)

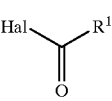

(V)

in which
$R^1$ is as defined above and
Hal represents halogen (in particular chlorine or bromine)
or
β) with carboxylic anhydrides of the formula (VI)

$R^1$—CO—O—CO—$R^1$ (VI)

in which
$R^1$ is as defined above,
if appropriate in the presence of a diluent and if appropriate in the presence of an acid binder;
(E) that the compounds of the formulae (I-1-c) to (I-3-c) shown above in which $R^2$, V, W, M, X, Y and Z are each as defined above and L represents oxygen are obtained when compounds of the formulae (I-1-a) to (I-3-a) shown above in which V, W, X, Y and Z are each as defined above are in each case reacted
with chloroformic esters or chloroformic thioesters of the formula (VII)

$R^2$—M—CO—Cl (VII)

in which
$R^2$ and M are each as defined above,
if appropriate in the presence of a diluent and if appropriate in the presence of an acid binder;

(F) that compounds of the formulae (I-1-c) to (I-3-c) shown above in which $R^2$, V, W, M, X, Y and Z are each as defined above and L represents sulphur are obtained when compounds of the formulae (I-1-a) to (I-3-a) shown above in which V, W, X, Y and Z are each as defined above are in each case reacted with chloromonothioformic esters or chlorodithioformnic esters of the formula (VIII)

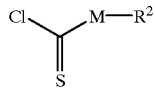
(VII)

in which
M and $R^2$ are each as defined above,
if appropriate in the presence of a diluent and if appropriate in the presence of an acid binder, (G) that compounds of the formulae (I-1-d) to (I-3-d) shown above in which $R^3$, V, W, X, Y and Z are each as defined above are obtained when compounds of the formulae (I-1-a) to (I-3-a) shown above in which V, W, X, Y and Z are each as defined above are in each case reacted with sulphonyl chlorides of the formula (IX)

$$R^3-SO_2-Cl \quad (IX)$$

in which
$R^3$ is as defined above,
if appropriate in the presence of a diluent and if appropriate in the presence of an acid binder, (H) that compounds of the formulae (I-1-e) to (I-3-e) shown above in which L, $R^4$, $R^5$, V, W, X, Y and Z are each as defined above are obtained when compounds of the formulae (I-1-a) to (I-3-a) shown above in which V, W, X, Y and Z are each as defined above are in each case reacted with phosphorus compounds of the formula (X)

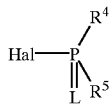
(X)

in which
L, $R^4$ and $R^5$ are each as defined above and
Hal represents halogen (in particular chlorine or bromine),
if appropriate in the presence of a diluent and if appropriate in the presence of an acid binder, (I) that compounds of the formulae (I-1-f) to (I-3-f) shown above in which E, V, W, X, Y and Z are each as defined above are obtained when compounds of the formulae (I-1-a) to (I-3-a) in which V, W, X, Y and Z are each as defined above are in each case reacted with metal compounds or amines of the formuale (XI) or (XII)

$$Me(OR^{10})_t \quad (XI)$$

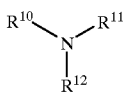
(XII)

in which
Me represents a mono- or divalent metal (preferably an alkali metal or alkaline earth metal, such as lithium, sodium, potassium, magnesium or calcium),
t represents the number 1 or 2 and
$R^{10}$, $R^{11}$, $R^{12}$ independently of one another each represent hydrogen or alkyl (preferably $C_1$–$C_8$-alkyl),
if appropriate in the presence of a diluent, (J) that compounds of the formulae (I-1-g) to (I-3-g) shown above in which L, $R^6$, $R^7$, V, W, X, Y and Z are each as defined above are obtained when compounds of the formulae (I-1-a) to (I-3-a) shown above in which V, W, X, Y and Z are each as defined above are in each case reacted α) with isocyanates or isothiocyanates of the formula (XIII)

$$R^6-N=C=L \quad (XIII)$$

in which
$R^6$ and L are each as defined above,
if appropriate in the presence of a diluent and if appropriate in the presence of a catalyst or β) with carbamoyl chlorides or thiocarbamoyl chlorides of the formula (XIV)

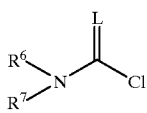
(XIV)

in which
L, $R^6$ and $R^7$ are each as defined above,
if appropriate in the presence of a diluent and if appropriate in the presence of an acid binder.

Furthermore, it has been found that the novel compounds of the formula (I) have very good activity as pesticides, preferably as insecticides, acaricides and herbicides, and that they are additionally frequently very well tolerated by plants, in particular by crop plants.

The formula (I) provides a general definition of the compounds according to the invention. Preferred substituents and/or ranges of the radicals listed in the formulae mentioned herein above and herein below are illustrated below:

V preferably represents hydrogen, halogen, $C_1$–$C_6$-alkyl or $C_1$–$C_6$-alkoxy, W preferably represents hydrogen, nitro, cyano, halogen, $C_1$–$C_6$-alkyl, $C_2$–$C_6$-alkenyl, $C_2$–$C_6$-alkinyl, $C_1$–$C_6$-alkoxy, $C_1$–$C_4$-halogenoalkyl, $C_1$–$C_4$-halogenoalkoxy or preferably represents in each case optionally halogen-, $C_1$–$C_6$-alkyl, $C_1$–$C_6$-alkoxy, $C_1$–$C_4$-halogenoalkyl, $C_1$–$C_4$-halogenoalkoxy, nitro- or cyano-substituted phenyl, phenoxy, phenylthio, phenyl-$C_1$–$C_4$-alkoxy or phenyl-$C_1$–$C_4$-alkylthio, X preferably represents halogen, $C_1$–$C_6$-alkyl, $C_2$–$C_6$-alkenyl, $C_2$–$C_6$-alkinyl, $C_1$–$C_6$-alkoxy, $C_1$–$C_4$-halogenoalkyl, $C_1$–$C_4$-halogenoalkoxy, cyano, nitro or preferably represents in each case optionally halogen, $C_1$–$C_6$-alkyl, $C_1$–$C_6$-alkoxy, $C_1$–$C_4$-halogenoalkyl, $C_1$–$C_4$-halogenoalkoxy, nitro- or cyano-substituted phenyl, phenoxy, phenylthio, phenyl-$C_1$–$C_4$-alkoxy or phenyl-$C_1$–$C_4$-alkylthio.

Y preferably represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

Z preferably represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, hydroxy, cyano, nitro or preferably represents in each case optionally halogen, $C_1$–$C_4$-alkyl, $C_1$–$C_4$-alkoxy, $C_1$–$C_4$-halogenoalkyl, $C_1$–$C_4$-halogenoalkoxy, nitro- or cyano-substituted phenoxy, phenylthio, thiazolyloxy, pyridinyloxy, pyrimidyloxy, pyrazolyloxy, phenyl-$C_1$–$C_4$-alkyloxy or phenyl-$C_1$–$C_4$-alkylthio or Y and Z together with the linking carbon atoms preferably represent in each case optionally halogen-, $C_1$–$C_6$-alkyl-, $C_1$–$C_6$-alkoxy- or $C_1$–$C_4$-halogenoalkyl-substituted $C_3$–$C_5$-alkanediyl or $C_3$–$C_5$-alkenediyl in which optionally one to three members may be replaced independently of one another by oxygen, sulphur, nitrogen or a carbonyl group, or W and Z together with the linking carbon atoms preferably represent in each case optionally halogen-, $C_1$–$C_6$-alkyl-, $C_1$–$C_6$-alkoxy- or $C_1$–$C_4$-halogenoalkyl-substituted $C_3$–$C_5$-alkanediyl or $C_3$–$C_5$-alkenediyl in which one to three members may be replaced independently of one another by oxygen, sulphur, nitrogen or a carbonyl group.

Het preferably represents one of the groups (1)
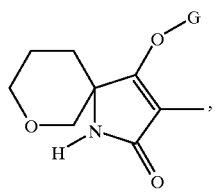

(2)
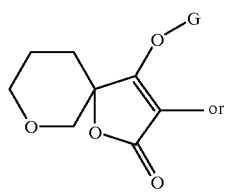

(3)
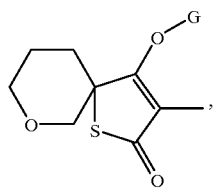

G preferably represents hydrogen (a) or preferably represents one of the groups (b)

(c)
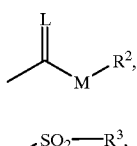

(d)
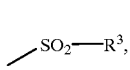

(e)
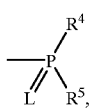

(f)
E, or (g)
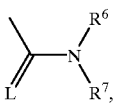

(in particular represents (a), (b) or (c))
in which
E represents a metal ion equivalent or an ammonium ion,
L represents oxygen or sulphur and
M represents oxygen or sulphur.

$R^1$ preferably represents in each case optionally halogen- or cyano-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl or preferably represents optionally halogen-, $C_1$–$C_6$-alkyl- or $C_1$–$C_6$-alkoxy-substituted $C_3$–$C_8$-cycloalkyl in which optionally one or two not directly adjacent methylene groups are replaced by oxygen and/or sulphur, preferably represents optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulfonyl-substituted phenyl, preferably represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, represents optionally halogen- or $C_1$–$C_6$-alkyl-substituted 5- or 6-membered hetaryl having one or two heteroatoms from the group consisting of oxygen, sulphur and nitrogen, for example pyrazolyl, thiazolyl, pyridyl, primidyl, furamyl or thienyl, preferably represents optionally halogen- or $C_1$–$C_6$-alkyl-substituted phenoxy-$C_1$–$C_6$-alkyl or preferably represents optionally halogen-, amino- or $C_1$–$C_6$-alkyl-substituted 5-or 6-membered hetaryloxy-$C_1$–$C_6$-alkyl having one or two heteroatoms from the group consisting of oxygen, sulphur and nitrogen, for example pyridyloxy-$C_1$–$C_6$-alkyl, pyrimidyl-$C_1$–$C_6$-alkyl or thiazolyloxy-$C_1$–$C_6$-alkyl).

$R^2$ preferably represents in each case optionally halogen- or cyano-substituted $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, preferably represents optionally halogen-, $C_1$–$C_6$-alkyl- or $C_1$–$C_6$-alkoxy-substituted $C_3$–$C_8$-cycloalkyl or preferably represents in each case optionally halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl.

$R^3$ preferably represents optionally halogen-substituted $C_1$–$C_8$-alkyl or preferably represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl.

$R^4$ and $R^5$ independently of one another each preferably represent in each case optionally halogen-substituted $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_3$–$C_8$-alkenylthio or preferably represent in each case optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, phenoxy or phenylthio.

$R^6$ and $R^7$ independently of one another each preferably represent hydrogen, preferably represent in each case optionally halogen- or cyano-substituted $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, preferably represent in each case optionally halogen-, $C_1$–$C_8$-alkyl-, $C_1$–$C_8$-halogenoalkyl or $C_1$–$C_8$-alkoxy-substituted phenyl or benzyl or together preferably represent an optionally $C_1$–$C_6$-alkyl-substituted $C_3$–$C_6$-alkylene radical in which optionally one methylene group is replaced by oxygen or sulphur.

V particularly preferably represents hydrogen, fluorine, chlorine, bromine, $C_1$–$C_4$-alkyl or $C_1$–$C_4$-alkoxy.

W particularly preferably represents hydrogen, nitro, cyano, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy or particularly preferably represents in each case optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenyl, phenoxy or benzyloxy.

X particularly preferably represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano, nitro or particularly preferably represents in each case optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenyl, phenoxy or benzyloxy.

Y particularly preferably represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

Z particularly preferably represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, hydroxyl, cyano, nitro or particularly preferably represents in each case optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenoxy or benzyloxy or Y and Z together with the linking carbon atoms particularly preferably represent in each case optionally fluorine-, chlorine-, bromine-, $C_1$–$C_4$-alkyl-, $C_1$–$C_4$-alkoxy- or $C_1$–C2-halogenoalkyl-substituted $C_3$–$C_4$-alkanediyl or $C_3$–$C_4$-alkenediyl in which optionally one or two not directly adjacent members may be replaced independently of one another by oxygen, sulphur or nitrogen, or W and Z together with the linking carbon atoms particularly preferably represent in each case optionally fluorine-, chlorine-, bromine-, $C_1$–$C_4$-alkyl-, $C_1$–$C_4$-alkoxy- or $C_1$–$C_2$-halogenoalkyl-substituted $C_3$–$C_4$-alkanediyl or $C_3$–$C_4$-alkenediyl in which one or two not directly adjacent members may be replaced independently of one another by oxygen, sulphur or nitrogen.

Het particularly preferably represents one of the groups

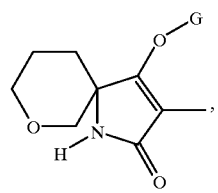

(1)

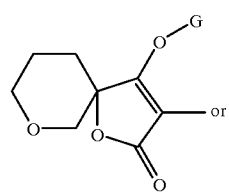

(2) or

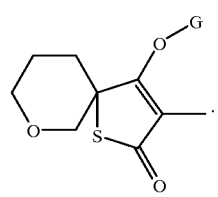

(3).

G particularly preferably represents hydrogen (a) or particularly preferably represents one of the groups

(b)

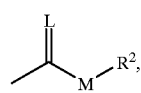

(c)

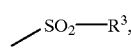

(d)

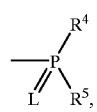

(e)

E, or (f)

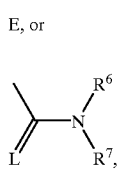

(g)

(in particular represents (a), (b) or (c))
in which
E represents a metal ion equivalent or an ammonium ion, L represents oxygen or sulphur and M represents oxygen or sulphur.

$R^1$ particularly preferably represents in each case optionally fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl or particularly preferably represents optionally fluorine-, chlorine-, $C_1$–$C_5$-alkyl- or $C_1$–$C_5$-alkoxy-substituted $C_3$–$C_7$-cycloalkyl in which optionally one or two not directly adjacent methylene groups are replaced by oxgyen and/or sulphur, particularly preferably represents optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-substituted phenyl, particularly preferably represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, particularly preferably represents in each case optionally fluorine-, chlorine-, bromine- or $C_1$–$C_4$-alkyl-substituted pyrazolyl, thiazolyl, pyridyl, pyrimidyl, furanyl or thienyl, particularly preferably represents optionally fluorine-, chlorine-, bromine- or $C_1$–$C_4$-alkyl-substituted phenoxy-$C_1$–$C_5$-alkyl or particularly preferably represents in each case optionally fluorine-, chlorine-, bromine-, amino- or $C_1$–$C_4$-alkyl-substituted pyridyloxy-$C_1$–$C_5$-alkyl, pyrimidyloxy-$C_1$–$C_5$-alkyl or thiazolyloxy-$C_1$–$C_5$-alkyl.

$R^2$ particularly preferably represents in each case optionally fluorine- or chlorine-substituted $C_1$–$C_{16}$-alkyl, $C_2$-$C_{16}$-alkenyl, $C_1$–$C_6$-alkoxy-$C_2$–$C_6$-alkyl or poly-$C_1$–$C_6$-alkoxy-$C_2$–$C_6$-alkyl, particularly preferably represents optionally fluorine-, chlorine-, $C_1$–$C_4$-alkyl- or $C_1$–$C_4$-alkoxy-substituted $C_3$–$C_7$-cycloalkyl or particularly preferably represents in each case optionally fluorine-, chlorine-, bromine-, cyano-, nitro-, $C_1$–$C_4$-alkyl-, $C_1$–$C_3$-alkoxy-, $C_1$–$C_3$-halogenoalkyl- or $C_1$–$C_3$-halogenoalkoxy-substituted phenyl or benzyl.

$R^3$ particularly preferably represents optionally fluorine- or chlorine-substituted $C_1$–$C_6$-alkyl or particularly preferably represents in each case optionally fluorine-, chlorine-, brornine-, $C_1$–$C_4$-alkyl-, $C_1$–$C_4$-alkoxy-, $C_1$–$C_2$-halogenoalkoxy-, $C_1$–$C_2$-halogenoalkyl-, cyano- or nitro-substituted phenyl or benzyl.

$R^4$ and $R^5$ independently of one another each particularly preferably represent in each case optionally fluorine- or chlorine-substituted $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio or particularly preferably represent in each case optionally fluorine-, chlorine-, bromine-, nitro-, cyano-, $C_1$–$C_3$-alkoxy-, $C_1$–$C_3$-halogenoalkoxy-, $C_1$–$C_3$-alkylthio-, $C_1$–$C_3$-halogenoalkylthio-, $C_1$–$C_3$-alkyl or $C_1$–$C_3$-halogenoalkyl-substituted phenyl, phenoxy or phenylthio.

$R^6$ and $R^7$ independently of one another each particularly preferably represent hydrogen, particularly preferably represent in each case optionally fluorine-, or chlorine-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, particularly preferably represent in each case optionally fluorine-, chlorine-, brornine-, $C_1$–$C_5$-halogenoalkyl-, $C_1$–$C_5$-alkyl- or $C_1$–$C_5$-alkoxy-substituted phenyl or benzyl, or together particularly preferably represent an optionally $C_1$–$C_4$-alkyl-substituted $C_3$–$C_6$-alkylene radical in which optionally one methylene group is replaced by oxygen or sulphur.

V very particularly preferably represents hydrogen, fluorine, chlorine, bromine, methyl, ethyl, propyl, iso-propyl, tert-butyl, methoxy, ethoxy, propoxy or iso-propoxy.

W very particularly preferably represents hydrogen, nitro, cyano, fluorine, chlorine, bromine, methyl, ethyl, propyl, n-butyl, iso-propyl, iso-butyl, methoxy, ethoxy, propoxy, iso-propoxy, trifluoromethyl, difluoromethoxy, trifluoromethoxy, phenyl or benzyloxy.

X very particularly preferably represents fluorine, chlorine, bromine, methyl, ethyl, propyl, butyl, iso-butyl, iso-propyl, methoxy, ethoxy, propoxy, iso-propoxy, trifluoromethyl, trifluoromethoxy, difluoromethoxy, cyano, nitro, phenyl or benzyloxy.

Y very particularly preferably represents hydrogen, fluorine, chlorine, bromine, methyl, ethyl, propyl, iso-propyl, n-butyl, iso-butyl, tert-butyl, methoxy, ethoxy, propoxy, iso-propoxy, trifluoromethyl, trifluoromethoxy, difluoromethoxy, cyano or nitro.

Z very particularly preferably represents hydrogen, fluorine, chlorine, bromine, methyl, ethyl, propyl, butyl, iso-butyl, iso-propyl, tert-butyl, methoxy, ethoxy, propoxy, iso-propoxy, trifluoromethyl, trifluoromethoxy, difluoromethoxy, cyano or nitro or Y and Z together with the linking carbon atoms very particularly preferably represent optionally fluorine-, chlorine-, methyl-, ethyl-, propyl-, iso-propyl-, methoxy-, ethoxy-, propoxy-, iso-propoxy- or trifluoromethyl-substituted $C_3$–$C_4$-alkanediyl in which optionally two not directly adjacent members are replaced by oxygen or W and Z together with the linking carbon atoms very particularly preferably represent optionally fluorine-, chlorine-, methyl-, ethyl-, propyl-, iso-propyl-, methoxy-, ethoxy-, propoxy-, iso-propoxy- or trifluoromethyl-substituted $C_3$–$C_4$-alkanediyl in which optionally two not directly adjacent members are replaced by oxygen.

Het very particularly preferably represents one of the groups (1)

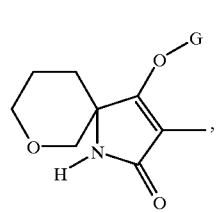

-continued

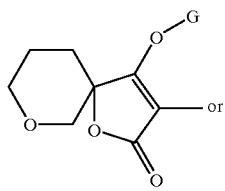
(2)
or

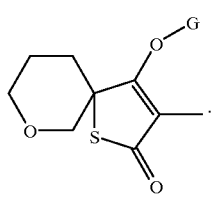
(3)

G very particularly preferably represents hydrogen (a) or very particularly preferably represents one of the groups

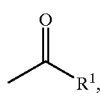
(b)

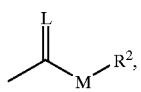
(c)

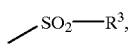
(d)

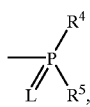
(e)

E, or

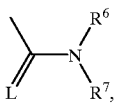
(g)

(in particular represents (a), (b) or (c))
in which
E represents a metal ion equivalent or an ammonium ion,
L represents oxygen or sulphur and
M represents oxygen or sulphur.

$R^1$ very particularly preferably represents in each case optionally chlorine- or fluorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl or very particularly preferably represents optionally fluorine-, chlorine-, methyl-, ethyl-, n-propyl-, i-propyl-, n-butyl-, i-butyl-, tert-butyl-, methoxy-, ethoxy-, n-propoxy- or iso-propoxy-substituted $C_3$–$C_6$-cycloalkyl, in which optionally one or two not directly adjacent methylene groups are replaced by oxygen and/or sulphur,
very particularly preferably represents optionally fluorine-, chlorine-, bromine-, cyano-, nitro-, methyl-, ethyl-, n-propyl-, i-propyl-, methoxy-, ethoxy-, trifluoromethyl-, trifluoromethoxy-, methylthio-, ethylthio-, methylsulphonyl- or ethylsulphonyl-substituted phenyl,
very particularly preferably represents optionally fluorine-, chlorine-, bromine-, methyl-, ethyl-, n-propyl-, i-propyl-, methoxy-, ethoxy-, trifluoromethyl- or trifluoromethoxy-substituted benzyl,
very particularly preferably represents in each case optionally fluorine-, chlorine-, bromine-, methyl- or ethyl-substituted furanyl, thienyl or pyridyl, very particularly preferably represents optionally fluorine-, chlorine-, methyl- or ethyl-substituted phenoxy-$C_1$–$C_4$-alkyl or
very particularly preferably represents in each case optionally fluorine-, chlorine-, amino-, methyl- or ethyl-substituted pyridyloxy-$C_1$–$C_4$-alkyl, pyrimidyloxy-$C_1$–$C_4$-alkyl or thiazolyloxy-$C_1$–$C_4$-alkyl.

$R^2$ very particularly preferably represents in each case optionally fluorine- or chlorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl,
very particularly preferably represents optionally fluorine-, chlorine-, methyl-, ethyl-, n-propyl, iso-propyl- or methoxy-substituted $C_3$–$C_6$-cycloalkyl,
or very particularly preferably represents in each case optionally fluorine-, chlorine-, cyano-, nitro-, methyl-, ethyl-, n-propyl-, i-propyl-, methoxy-, ethoxy-, trifluoromethyl- or trifluoromethoxy-substituted phenyl or benzyl.

$R^3$ very particularly preferably represents in each case optionally fluorine- or chlorine-substituted methyl, ethyl, propyl, iso-propyl, n-butyl, tert-butyl, or very particularly preferably represents in each case optionally fluorine-, chlorine-, bromine-, methyl-, ethyl-, iso-propyl-, tert-butyl-, methoxy-, ethoxy-, iso-propoxy-, trifluoromethyl-, trifluoromethoxy-, cyano- or nitro-substituted phenyl or benzyl.

$R^4$ and $R^5$ independently of one another each very particularly preferably represent in each case optionally fluorine- or chlorine-substituted $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio or very particularly preferably represent in each case optionally fluorine-, chlorine-, bromine-, nitro-, cyano-, methyl-, methoxy-, trifluoromethyl- or trifluoromethoxy-substituted phenyl, phenoxy or phenylthio.

$R^6$ and $R^7$ independently of one another very particularly preferably represent hydrogen, very particularly preferably represent in each case optionally fluorine- or chlorine-substituted $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, very particularly preferably represent in each case optionally fluorine-, chlorine-, bromine-, methyl-, methoxy- or trifluoromethyl-substituted phenyl or benzyl, or together very particularly preferably represent an optionally methyl- or ethyl-substituted $C_5$–$C_6$-alkylene radical in which optionally one methylene group is replaced by oxygen or sulphur.

The abovementioned general or preferred definitions of radicals or illustrations can be combined with each other as desired, that is to say combinations between the ranges and preferred ranges in question are also possible. They apply both to the end products and, correspondingly, to the starting materials and intermediates.

Preference according to the invention is given to those compounds of the formula (I) which contain a combination of the definitions given above as being preferred (preferable).

Particular preference according to the invention is given to those compounds of the formula (I) which contain a combination of the definitions given above as being particularly preferred.

Very particular preference according to the invention is given to those compounds of the formula (I) which contain a combination of the definitions given above as being very particularly preferred.

Saturated or unsaturated hydrocarbon radicals, such as alkyl or alkenyl, may be, also in combination with heteroatoms such as, for example, in alkoxy, in each case straight-chain or branched as far as is possible.

Optionally substituted radicals may be mono- or polysubstituted, it being possible for the substituents in the case of polysubstitutions to be identical or different.

In addition to the compounds mentioned in the Preparation Examples, the following compounds of the formula (I-1-a) may be mentioned specifically:

TABLE 1

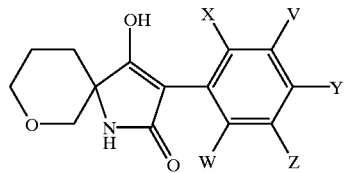

(I-1-a)

| V | X | W | Y | Z |
|---|---|---|---|---|
| H | Br | H | Cl | H |
| H | Cl | H | Br | H |
| H | Cl | H | Cl | H |
| H | Cl | H | F | H |
| H | F | H | Cl | H |
| H | Cl | H | OCH$_3$ | H |
| H | Cl | H | CH$_3$ | H |
| H | OCH$_3$ | H | Cl | H |
| H | OCH$_3$ | H | OCH$_3$ | H |
| H | CH$_3$ | H | Cl | H |
| H | CH$_3$ | H | F | H |
| H | CH$_3$ | H | OCH$_3$ | H |
| H | CH$_3$ | H | t-C$_4$H$_9$ | H |
| H | CH$_3$ | H | CH$_3$ | H |
| H | Cl | Cl | H | H |
| H | Cl | F | H | H |
| H | Cl | OCH$_3$ | H | H |
| H | Cl | CH$_3$ | H | H |
| H | Cl | OC$_2$H$_5$ | H | H |
| H | OCH$_3$ | OCH$_3$ | H | H |
| H | CH$_3$ | CH$_3$ | H | H |
| H | Br | CH$_3$ | Br | H |
| H | Cl | Cl | CH$_3$ | H |
| H | CH$_3$ | Br | CH$_3$ | H |
| H | CH$_3$ | Cl | CH$_3$ | H |
| H | CH$_3$ | OCHF$_2$ | CH$_3$ | H |
| H | CH$_3$ | OCH$_2$CF$_3$ | CH$_3$ | H |
| H | CH$_3$ | OC$_2$H$_5$ | CH$_3$ | H |
| H | CH$_3$ | OCH$_3$ | CH$_3$ | H |
| H | CH$_3$ | CH$_3$ | CH$_3$ | H |
| H | Br | Br | CH$_3$ | H |
| H | Cl | Cl | CH$_3$ | H |
| H | C$_2$H$_5$ | C$_2$H$_5$ | Br | H |
| H | CH$_3$ | CH$_3$ | Br | H |
| H | CH$_3$ | CH$_3$ | OCH$_3$ | H |
| H | Br | Cl | CH$_3$ | H |
| H | Br | CH$_3$ | Cl | H |
| H | Cl | CH$_3$ | Br | H |
| H | C$_2$H$_5$ | Br | CH$_3$ | H |
| H | CH$_3$ | O—C$_3$H$_7$ | CH$_3$ | H |
| H | CH$_3$ | O—Bz* | CH$_3$ | H |

TABLE 1-continued (I-1-a)

| V | X | W | Y | Z |
|---|---|---|---|---|
| H | CH$_3$ | CH$_3$ | Cl | H |
| H | CH$_3$ | Ph* | CH$_3$ | H |
| H | Cl | H | Cl | Cl |
| H | CH$_3$ | H | CH$_3$ | CH$_3$ |
| H | CH$_3$ | H | Cl | CH$_3$ |
| H | Br | H | Cl | CH$_3$ |
| H | Br | H | CH$_3$ | CH$_3$ |
| H | Cl | H | Br | CH$_3$ |
| H | Cl | H | Cl | CH$_3$ |
| H | CH$_3$ | H | Br | CH$_3$ |
| H | Cl | H | Cl | F |
| H | Cl | H | —O—CF$_2$—O— | |
| H | Br | H | —(CH$_2$)$_3$— | |
| H | Cl | H | CH$_3$ | Cl |
| H | CH$_3$ | H | H | H |
| H | Cl | H | H | H |
| H | Br | H | H | H |
| H | O—Bz | H | H | H |
| H | CF$_3$ | H | H | H |
| H | OCH$_3$ | H | H | H |
| H | CH$_3$ | CH$_3$ | CH$_3$ | CH$_3$ |
| CH$_3$ | CH$_3$ | H | CH$_3$ | CH$_3$ |
| CH$_3$ | CH$_3$ | CH$_3$ | H | CH$_3$ |
| H | Br | Br | —(CH$_2$)$_3$— | |
| H | CH$_3$ | CH$_3$ | CH$_3$ | F |
| H | CH$_3$ | CH$_3$ | CH$_3$ | Cl |
| H | CH$_3$ | CH$_3$ | CH$_3$ | Br |
| H | CH$_3$ | CH$_3$ | H | Cl |
| H | CH$_3$ | CH$_3$ | H | Br |
| H | Cl | Cl | H | Br |
| CH$_3$ | CH$_3$ | CH$_3$ | CH$_3$ | CH$_3$ |

*Bz = benzyl; Ph = phenyl

In addition to the compounds mentioned in the Preparation Examples, the following compounds of the formula (I-2-a) may be mentioned specifically.

Table 2

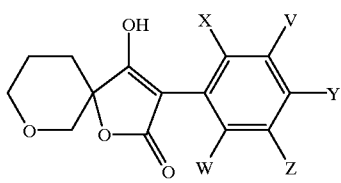

(I-2-a)

in which

V, W, X, Y and Z are each as defined in Table 1.

In addition to the compounds mentioned in the Preparation Examples, the following compounds of the formula (I-3-a) may be mentioned specifically.

Table 3

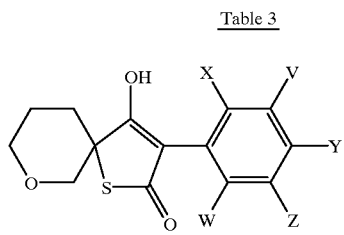
(I-3-a)

in which

V, W, X, Y and Z are each as defined in Table 1.

Using according to process (A) N-[(4-chloro-2,6-dimethyl)-phenylacetyl]-3-amino-3-carboxyethyl-tetrahydropyran as starting material, the course of the process according to the invention can be represented by the following equation:

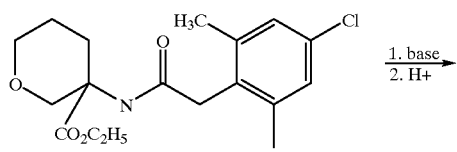

Using according to process (B) O-[(2-chloro-6-methyl)-phenylacetyl]-3-hydroxy-3-carboxyethyl-tetrahydropyran as starting material, the course of the process according to the invention can be represented by the following equation:

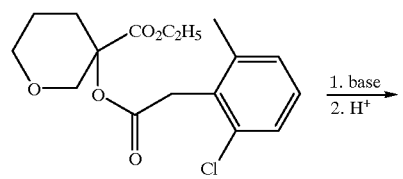

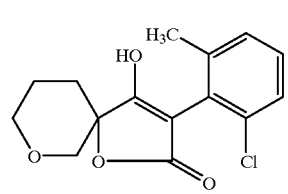

Using according to process (c) ethyl 2-[(2-chloro-4,6-dimethyl)-phenyl]-4-(4-methoxy)-benzylmercapto-4,4-methyleneoxypropyl-3-oxo-valerate, the course of the process according to the invention can be represented by the following equation:

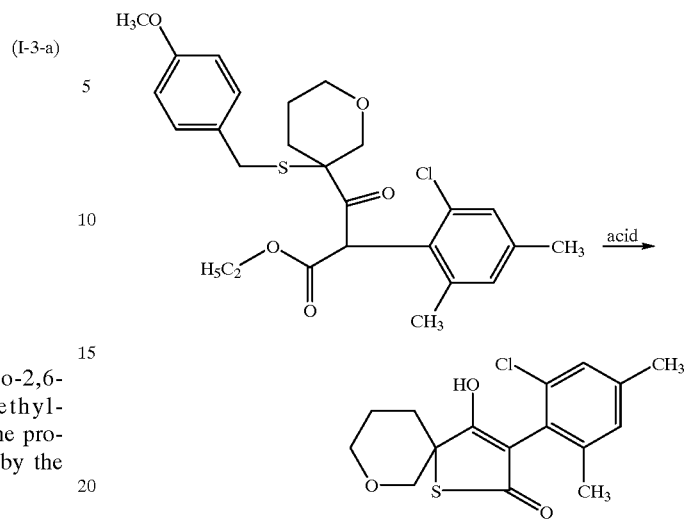

Using according to process (Dα) 3-[(2-chloro-4-methyl)-phenyl]-5,5-methyleneoxypropyl-pyrrolidine-2,4-dione and pivaloyl chloride as starting materials, the course of the process according to the invention can be represented by the following equation:

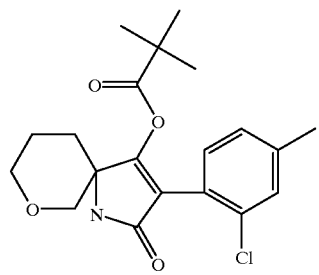

Using according to process (D) (Variant β) 3-[(2,4-dichloro)-phenyl]-4-hydroxy-5,5-methyleneoxypropyl-Δ³-dihydrofuran-2-one and acetic anhydride as starting materials, the course of the process according to the invention can be represented by the following equation:

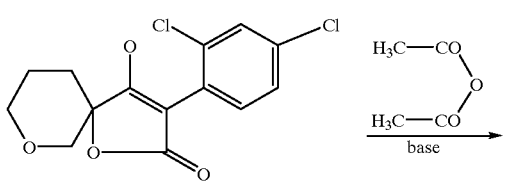

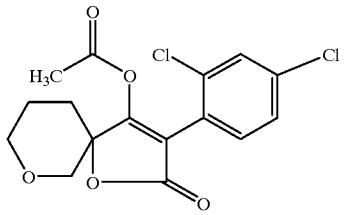

Using according to process (E) 8-[(2,4-dichloro)-phenyl]-5,5-methyleneoxypropyl-pyrrolidine-2,4-dione and ethoxyethyl chloroformate as starting materials, the course of the process according to the invention can be represented by the following equation:

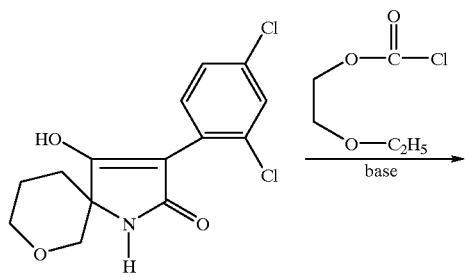

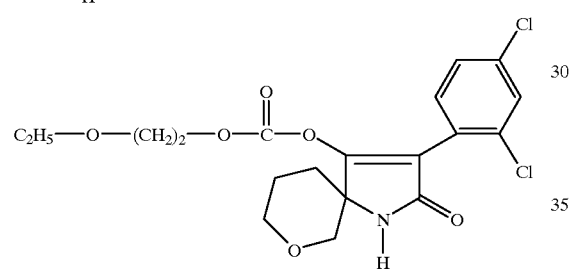

Using according to process (F) 3-[(2,6-dibromo-4-methyl)-phenyl]-4-hydroxy-5,5-methyleneoxypropyl-$\Delta^3$-dihydrofuran-2-one and methyl chloromonothioformate as starting materials, the course of the reaction can be represented as follows:

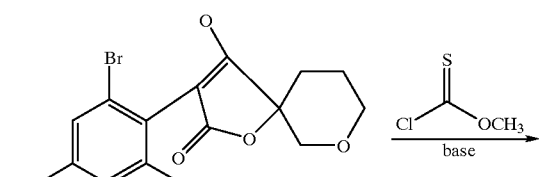

Using according to process (G) 2-[(2,4,6-trimethyl)-phenyl]-5,5-methyleneoxypropyl-pyrrolidine-2,4-dione and methanesulphonyl chloride as starting material, the course of the reaction can be represented by the following equation:

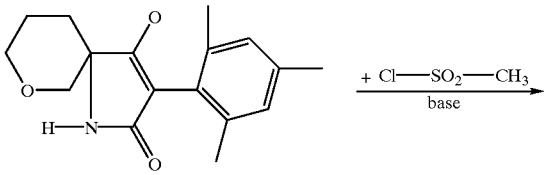

Using according to process (H) 2-[(4-bromo-2-chloro-6-methyl)-phenyl]-4-hydroxy-5,5-methyleneoxypropyl-$\Delta^3$-dihydrofuran-2-one and (2,2,2-trifluoroethyl) methanethiophosphonyl chloride as starting materials, the course of the reaction can be represented by the following equation:

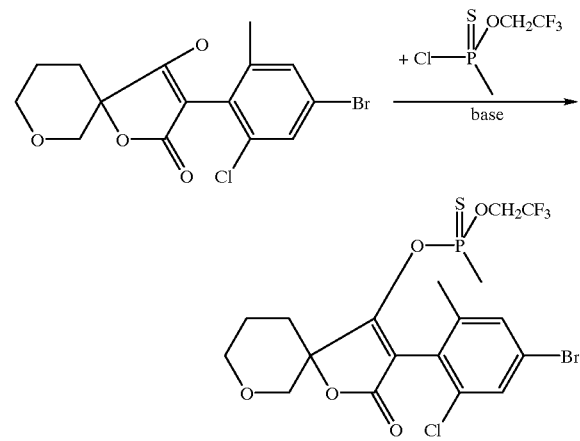

Using according to process (I) 3-[(2,4-dichloro)-6-methylphenyl]-5,5-methyleneoxypropyl-pyrrolidine-2,4-dione and NaOH as components, the course of the process according to the invention can be represented by the following equation:

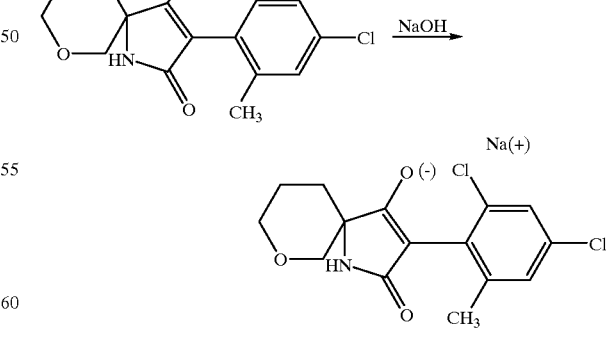

Using according to process (J) (variant α) 3-[(2-chloro-4-bromo-5-methyl)-phenyl]-4-hydroxy-5,5-methyleneoxypropyl-$\Delta^3$-dihydrofuran-2-one and ethylisocyanate as starting materials, the course of the reaction can be represented by the following equation:

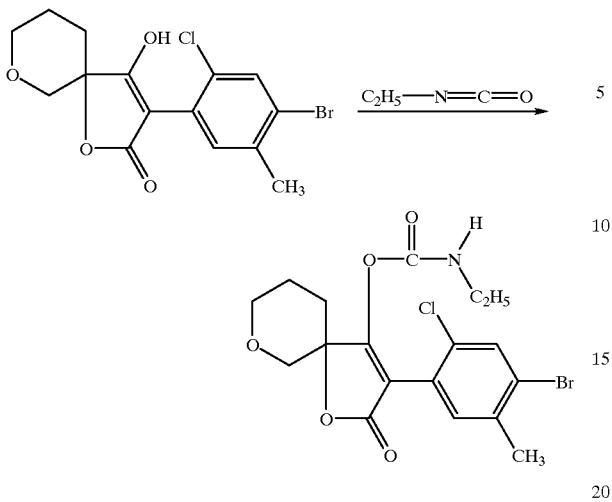

Using according to process (J) (variant β) 3-[(2-chloro-4,6-dimethyl)-phenyl]-5,5-methyleneoxypropyl-pyrrolidine-2,4-dione and dimethylcarbamidoyl chloride as starting materials, the course of the reaction can be represented by the following equation:

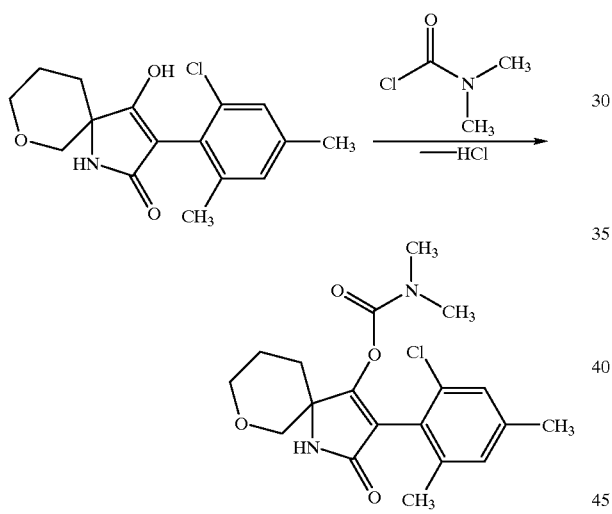

The compounds of the formula (II) required as starting materials in the process (A) according to the invention

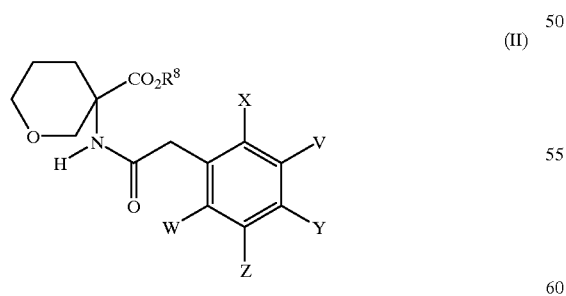

(II)

in which
V, W, X, Y, Z and $R^8$ are each as defined above
are novel.

The acylamino acid esters of the formula (II) are obtained, for example, when amino acid derivatives of the formula (XV)

(XV)

in which
$R^8$ is as defined above
are acylated with substituted phenylacetyl halides of the formula (XVI)

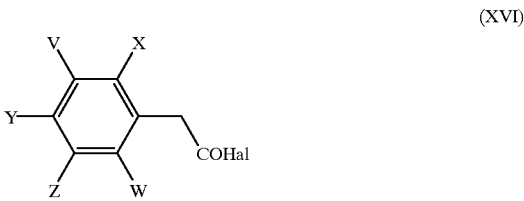

(XVI)

in which
V, W, X, Y and Z are each as defined above and
Hal represents chlorine or bromine
(Chem. Reviews 52, 237–416 (1953); Bhattacharya, Indian J. Chem. 6, 341–5, 1968),
or when acylamino acids of the formula (XVII)

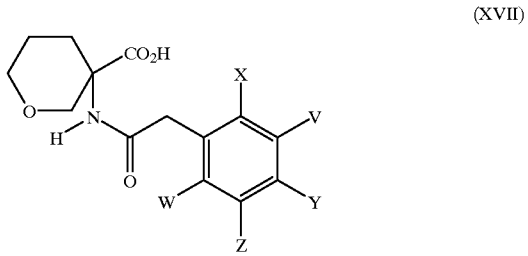

(XVII)

in which
V, W, X, Y and Z are each as defined above
are esterified (Chem. Ind. (London) 1568 (1968)).

The compounds of the formula (XVII)

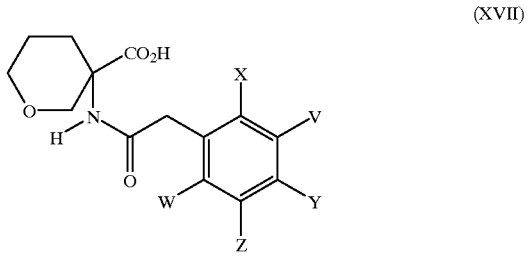

(XVII)

in which
V, W, X, Y and Z are each as defined above
are novel.

Compounds of the formula (XVII) are obtained, for example, when 3-amino-tetrahydropyran-3-carboxylic acid of the formula (XVIII)

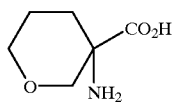
(XVIII)

is acylated according to Schotten-Baumann (Organikum, VEB Deutscher Verlag der Wissenschaften, Berlin 1977, p. 505) with substituted phenylacetyl halides of the formula (XVI)

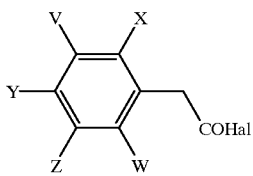
(XVI)

in which

V, W, X, Y and Z are each as defined above and

Hal represents chlorine or bromine.

Some of the compounds of the formula (XVI) are novel and can be prepared by known processes (cf., for example, WO 97/02 243, WO 97/01 535 and DE-196 13 171).

The compounds of the formula (XVI) are obtained, for example, by reacting substituted phenylacetic acids of the formula (XIX)

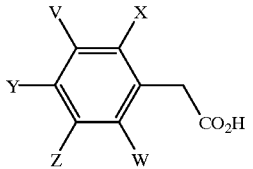
(XIX)

in which

V, W, X, Y and Z are each as defined above with halogenating agents (for example thionyl chloride, thionyl bromide, oxalyl chloride, phosgene, phosphorus trichloride, phosphorus tribromide or phosphorus pentachloride), if appropriate in the presence of a diluent (for example optionally chlorinated aliphatic or aromatic hydrocarbons such as toluene or methylene chloride) at temperatures of from −20° C. to 150° C., preferably of from −10° C. to 100° C.

Some of the compounds of the formula (XIX) are novel, they can be prepared by processes known from the literature (Organikum 15th edition, p. 533, VEB Deutscher Verlag der Wissenschaften, Berlin 1977, cf., for example, WO 97/02 243, WO 07/01 535 and DE-196 13 171). The compounds of the formula (XIX) are obtained, for example, by hydrolyzing substituted phenylacetic acids of the formula (XX)

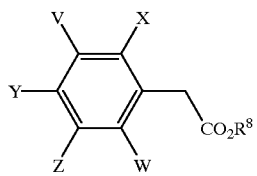
(XX)

in which

V, W, X, Y, Z and $R^8$ are each as defined above in the presence of an acid (for example an inorganic acid such as hydrochloric acid) or a base (for example an alkali metal hydroxide such as sodium hydroxide or potassium hydroxide) and, if appropriate, a diluent (for example an aqueous alcohol such as methanol or ethanol) at temperatures between 0° C. and 150° C., preferably between 20° C. and 100° C.

Some of the compounds of the formula (XX) are novel, they can be prepared by processes known in principle.

The compounds of the formula (XX) are obtained, for example, by reacting substituted 1,1,1-trichloro-2-phenylethanes of the formula (XXI)

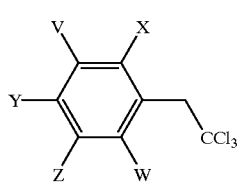
(XXI)

in which

V, W, X, Y and Z are each as defined above initially with alkoxides (for example alkali metal alkoxides such as sodium methoxide or sodium ethoxide) in the presence of a diluent (for example of the alcohol derived from the alkoxide) at temperatures between 0° C. and 150° C., preferably between 20° C. and 120° C. and subsequently reacting with an acid (preferably an inorganic acid, such as, for example, sulphuric acid) at temperatures between −20° C. and 150° C., preferably between 0° C. and 100° C., (cf. DE-3 314 249).

Some of the compounds of the formula (XXI) are novel, they can be prepared by processes known in principle.

The compounds of the formula (XXI) are obtained, for example, when anilines of the formula (XXII)

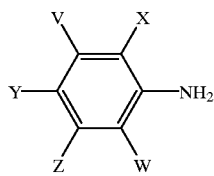
(XXII)

in which

V, W, X, Y and Z are each as defined above are reacted in the presence of an alkyl nitrite of the formula (XXIII)

$R^{13}$-ONO (XXIII)

in which $R^{13}$ represents alkyl, preferably $C_1$–$C_6$-alkyl, in the presence of copper (II) chloride and if appropriate in the presence of a diluent (for example an aliphatic nitrile such as acetonitrile) at a temperature of from −20° C. to 80° C., preferably from 0° C. to 60° C., with vinylidene chloride ($CH_2$=$CCl_2$).

Some of the compounds of the formula (XXII) are known. However, they can be prepared by processes known from the literature, for example by reducing the corresponding nitro compounds or by halogenating the anilines or acetanilines, followed by recleavage.

The compounds of the formula (XXIII) are known compounds of organic chemistry. Copper(II) chloride and vinylidene chloride have been known for a long time and are commercially available.

The compounds of the formula (XV) and (XVIII) are novel. They can be prepared by known processes (see, for example Compagnon, Ann. Chim. (Paris) [14] 5, p. 11–22, 23–27 (1970), L. Munday, J. Chem. Soc. 4372 (1961); J. T. Edward, C. Jitrangeri, Can. J. Chem. 53, 3339 (1975).

Furthermore, the starting materials of the formula (II)

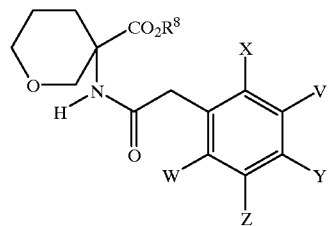

(II)

in which

V, W, X, Y, Z and $R^8$ are each as defined above used in the process (A) can be prepared when 3-amino-tetrahydropyran-3-carbonitrile of the formula (XXIV)

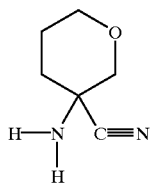

(XXIV)

is reacted with substituted phenylacetyl halides of the formula (XVI)

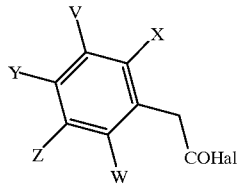

(XVI)

in which

V, W, X, Y, Z and Hal are each as defined above to give compounds of the formula (XXV)

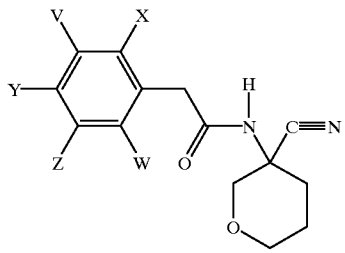

(XXV)

in which

V, W, X, Y and Z are each as defined above and these are subsequently subjected to acid alcoholysis.

The compounds of the formula (XXV) are also novel. The compounds of the formula (XXIV) are also novel (see Preparation Example).

The compounds of the formula (III)

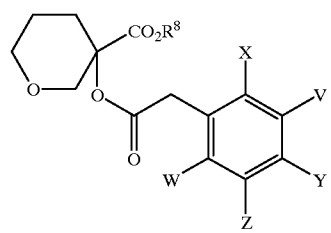

(III)

in which

V, W, X, Y, Z and $R^8$ are each as defined above required as starting materials in the process (B) according to the invention are novel.

They can be prepared in a simple manner by methods known in principle.

The compounds of the formula (III) are obtained, for example, when 3-hydroxy-tetrahydropyran-3-carboxylic esters of the formula (XXVI)

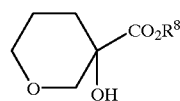

(XXVI)

in which $R^8$ is as defined above are acylated with substituted phenylacetyl halides of the formula (XVI)

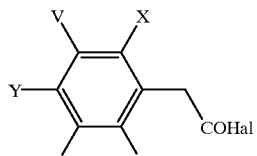

(XVI)

in which

V, W, X, Y, Z and Hal are each as defined above
(Chem. Reviews 52, 237–416 (1953)).

The 3-hydroxy-tetrahydropyran-3-carboxylic esters of the formula (XXVI) are novel. They are obtained, for example, by alcoholizing 3-hydroxy-tetrahydropyran-3-carbonitrile of the formula (XXVI-a) in the presence of acids, for example according to Pinner (see Preparation Example). The cyanohydrin is obtained, for example, by reacting tetrahydropyran-3-one with hydrocyanic acid.

The compounds of the formula (IV)

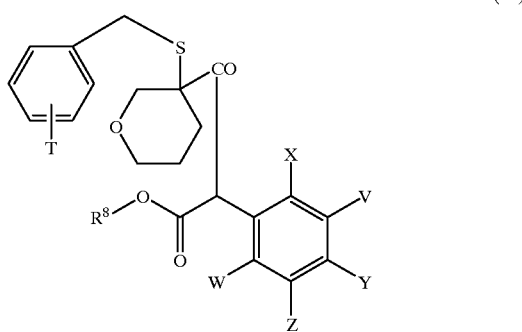

(IV)

in which

T, V, W, X, Y, Z and $R^8$ are each as defined above required as starting materials in the above process (C) are novel.

They can be prepared by methods known in principle.

The compounds of the formula (IV) are obtained, for example, when substituted phenylacetic esters of the formula (XX)

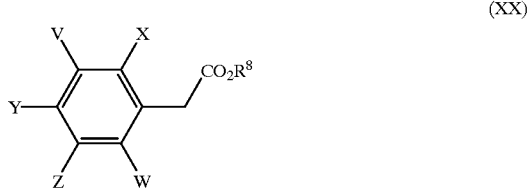

(XX)

in which

V, W, X, Y, $R^8$ and Z are each as defined above are acylated with 2-benzylthio-carbonyl halides of the formula (XXVII)

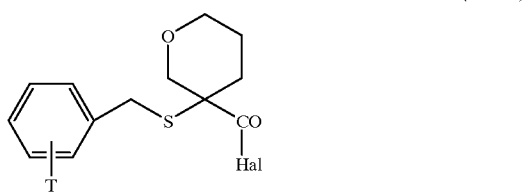

(XXVII)

in which

T is as defined above and

Hal represents halogen (in particular chlorine or bromine) in the presence of strong bases (see, for example, M. S. Chambers, E. J. Thomas, D. J. Williams, J. Chem. Soc. Chem. Commun., (1987), 1228).

The benzylthio-carbonyl halides of the formula (XXVII) are novel. They can be prepared by known processes (J. Antibiotics (1983), 26, 1589).

The acyl halides of the formula (V), carboxylic anhydrides of the formula (VI), chloroformic esters or chloroformic thioesters of the formula (VII), chloromonothioformic esters or chlorodithioformic esters of the formula (VIII), sulphonyl chlorides of the formula (IX), phosphorus compounds of the formula (X) and metal hydroxides, metal alkoxides or amines of the formula (XI) and (XII) and isocyanates of the formula (XIII) and carbamoyl chlorides of the formula (XIV) furthermore required as starting materials for carrying out the processes (D), (E), (F), (G), (H), (I) and (J) according to the invention are generally known compounds of organic or inorganic chemistry.

The compounds of the formulae (XVI), (XIX), (XX), (XXI) and (XXII) are furthermore known from the patent applications cited at the outset and/or can be prepared by methods given therein (cf. also WO 96/35 664, WO 97/01 535, WO 97/02 243 and DE-196 13 171).

The process (A) is characterized in that compounds of the formula (II) in which V, W, X, Y, Z and $R^8$ are each as defined above are subjected to an intramolecular condensation in the presence of a diluent and in the presence of a base.

Suitable diluents for use in the process (A) according to the invention are all organic solvents which are inert towards the reactants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols such as methanol, ethanol, propanol, iso-propanol, butanol, iso-butanol and tert-butanol.

Suitable bases (deprotonating agents) for use in the practice of the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltrialkyl($C_8$–$C_{10}$) ammonium chloride) or TDA 1 (=tris-(methoxyethoxyethyl)-amine). It is also possible to use alkali metals such as sodium or potassium. Furthermore, it is possible to use alkali metal and alkaline earth metal amides and hydrides, such as sodium amide, sodium hydride and calcium hydride, and moreover also alkali metal alkoxides, such as sodium methoxide, sodium ethoxide and potassium tert-butoxide.

When carrying out the process (A) according to the invention, the reaction temperature can be varied within a relatively wide range. In general, the reaction is carried out at temperatures between –75° C. and 200° C., preferably between –50° C. and 150° C.

The process (A) according to the invention is generally carried out under atmospheric pressure.

When carrying out the process (A) according to the invention, the reaction component of the formula (II) and the deprotonating base are generally employed in equimolar to about doubly-equimolar amounts. However, it is also possible to use one component or the other in a relatively large excess (upto 3 mol).

The process (B) is characterized in that compounds of the formula (m) in which V, W, X, Y, Z and $R^8$ are each as defined above are intramolecularly condensed in the presence of a diluent and in the presence of a base.

Suitable diluents for use in the process (B) according to the invention are all solvents which are inert towards the reactants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. Furthermore, it is possible to use alcohols such as methanol, ethanol, propanol, iso-propanol, butanol, iso-butanol and tert-butanol.

Suitable bases (deprotonating agents) for use in the practice of the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltrialkyl($C_8$–$C_{10}$) ammonium chloride) or TDA 1 (=tris-(methoxyethoxyethyl)-amine). It is also possible to use alkali metals such as sodium or potassium. Furthermore, it is possible to use alkali metal and alkaline earth metal amides and hydrides, such as sodium amide, sodium hydride and calcium hydride, and moreover also alkali metal alkoxides, such as sodium methoxide, sodium ethoxide and potassium tert-butoxide.

When carrying out the process (B) according to the invention, the reaction temperature can be varied within a relatively wide range. In general, the reaction is carried out at temperatures between –75° C. and 200° C., preferably between –50° C. and 150° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use one component or the other in a relatively large excess (upto 3 mol).

Process (C) is characterized in that compounds of the formula (IV) in which T, V, W, X, Y, Z and $R^8$ are each as defined above are intramolecularly cyclized in the presence of an acid and, if appropriate, in the presence of a diluent.

Suitable diluents for use in the process (C) according to the invention are all organic solvents which are inert towards the reactants. Preference is given to using hydrocarbons, such as toluene and xylene, furthermore halogenated hydrocarbons, such as dichloromethane, chloroform, ethylene chloride, chlorobenzene, dichlorobenzene, moreover polar solvents, such as dimethyl sulphoxide, sulpholane, dimethylformamide and N-methyl-pyrrolidone. Furthermore, it is also possible to use alcohols such as, methanol, ethanol, propanol, iso-propanol, butanol, iso-butanol, tert-butanol.

If appropriate, the acid used can also serve as diluent.

Suitable acids for use in the process (C) according to the invention are all customary inorganic and organic acids, such as, for example, hydrohalic acids, sulphuric acid, alkyl-, aryl-, and haloalkylsulphonic acids, and use is made in particular of halogenated alkylcarboxylic acids, such as, for example, trifluoroacetic acid.

When carrying out the process (C) according to the invention, the reaction temperature can be varied within a relatively wide range. In general, the reaction is carried out at temperatures between 0° C. and 250° C., preferably between 50° C. and 150° C.

The process (C) according to the invention is generally carried out under atmospheric pressure.

When carrying out the process (C) according to the invention, the reaction components of the formula (IV) and the acid are employed, for example, in equimolar amounts. However, it is also possible, if appropriate, to use catalytic amounts of the acid.

The process (Dα) is characterized in that compounds of the formulae (I-1-a) to (I-3-a) are in each case reacted with carbonyl halides of the formula (V), if appropriate in the presence of a diluent and if appropriate in the presence of an acid binder.

Suitable diluents for use in the process (Dα) according to the invention are all solvents which are inert towards the acyl halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylfonnamide, dimethyl sulphoxide and sulpholane. The hydrolytic stability of the acyl halide permitting, the reaction can also be carried out in the presence of water.

Suitable acid binders for the reaction according to process (Dα) according to the invention are all customary acid acceptors. Preference is given to using tertiary amines, such as triethylamine, pyridine, diazabicyclooctane (DABCO), diazabicycloundecene (DBU), diazabicyclononene (DBN), Hunig base and N,N-dimethyl-aniline, furthermore alkaline earth metal oxides, such as magnesium oxide and calcium oxide, and also alkali metal and alkaline earth metal carbonates, such as sodium carbonate, potassium carbonate and calcium carbonate and also alkalie metal hydroxides such as sodium hydroxide and potassium hydroxide.

The reaction temperature of the process (Dα) according to the invention can be varied within a relatively wide range. In general, the reaction is carried out at temperatures between –20° C. and +150° C., preferably between 0° C. and 100° C.

When carrying out the process (Dα) according to the invention, the starting materials of the formulae (I-1-a) to (I-3-a) and the carbonyl halide of the formula (V) are generally each employed in approximately equivalent amounts. However, it is also possible to employ a relatively large excess (upto 5 mol) of the carbonyl halide.

Work-up is carried out by customary methods.

The process (Dβ) is characterized in that compounds of the formulae (I-1-a) to (I-3-a) are each reacted with carboxylic anhydrides of the formula (VI), if appropriate in the presence of a diluent and if appropriate in the presence of an acid binder.

Suitable diluents for use in the process (Dβ) according to the invention are preferably those diluents which are also preferred when acyl halides are used. Additionally, a carboxylic anhydride employed in excess can also simultaneously act as diluent.

The acid binders which are, if appropriated added in the process (Dβ) are preferably those acid binders which are also preferred when acyl halides are used.

The reaction temperature in the process (Dβ) according to the invention can be varied within a relatively wide range. In general, the reaction is carried out at temperatures beween –20° C. and +150° C., preferably between 0° C. and 100° C.

When carrying out the process (Dβ) according to the invention, the starting materials of the formulae (I-1-a) to (I-3-a) and the carboxylic anhydride of the formula (VI) are generally each employed in approximately equivalent amounts. However, it is also possible to employ a relatively large excess (upto 5 mol) of carboxylic anhydride. Work-up is carried out by customary methods.

In general, diluent and excess carboxylic anhydride and also the carboxylic acid formed are removed by distillation or by washing with an organic solvent or with water.

The process (E) is characterized in that compounds of the formulae (I-1-a) to (I-3-a) are in each case reacted with chloroformic esters or chloroformic thiol esters of the formula (VII), if appropriate in the presence of a diluent and if appropriate in the presence of an acid binder.

Acid binders which are suitable for the process (E) according to the invention are all customary acid acceptors. Preference is given to using tertiary amines, such as triethylamine, pyridine, DABCO, DBU, DBN, Huinig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides such as sodium hydroxide and potassium hydroxide.

Suitable diluents for use in the process (E) according to the invention are all solvents which are inert towards the chloroformic esters or chloroformic thio esters. Preference is given to using hydrocarbons, such as benzine, benzene, toluene, xylene and tetralin, furthermore, halogenated hydrocarbons, such as methylene chloride, chloroform, carbon tetrachloride, chlorobenzene and o-dichlorobenzene, moreover ketones, such as acetone and methyl ispropyl ketone, furthermore ethers, such as diethyl ether, tetrahydrofuran and dioxane, additionally carboxylic esters, such as ethyl acetate, moreover nitrites such as acetonitrile and also strongly polar solvents, such as dimethylformamide, dimethyl sulphoxide and sulpholane.

When carrying out the process (E) according to the invention, the reaction temperature can be varied within a relatively wide range. In general, the reaction temperature is between $-20°$ C. and $+100°$ C., preferably between $0°$ C. and $50°$ C.

The process (E) according to the invention is generally carried out under atmospheric pressure.

When carrying out the process (E) according to the invention, the starting materials of the formulae (I-1-a) to (I-3-a) and the appropriate chloroformic ester or chloroformic thiol ester of the formula (VII) are generally each employed in approximately equivalent amounts. However, it is also possible to employ one component or the other in a relatively large excess (up to 2 mol). Work-up is carried out by customary methods. In general, precipitated salts are removed and the reaction mixture which remains is concentrated by removing the diluent under reduced pressure.

The process (F) according to the invention is characterized in that compounds of the formulae (I-1-a) to (I-3-a) are in each case reacted with compounds of the formula (VIII) in the presence of a diluent and, if appropriate, in the presence of an acid binder.

In the preparation process (F), approximately 1 mol of chloromonothioformic ester or chlorodithioformic ester of formula (VIII) per mole of starting material of the formulae (I-1-a) to (I-3-a) is reacted at 0 to $120°$ C., preferably at 20 to $60°$ C.

Diluents which may be added, if appropriate, are all inert polar organic solvents, such as ethers, amides, sulphones, sulphoxides, and also halogenoalkanes.

Preference is given to using dimethyl sulphoxide, tetrahydrofuran, dimethylformamide, ethyl acetate or methylene chloride.

If, in a preferred embodiment, the enolate salt of the compounds (I-1-a) to (I-3-a) is prepared by addition of strong deprotonating agents such as, for example, sodium hydride or potassium tert-butoxide, the addition of acid binders can be dispensed with.

Suitable bases for use in the process (F) are all customary proton acceptors. Preference is given to using alkali metal hydrides, alkali metal alkoxides, alkali metal or alkaline earth metal carbonates or bicarbonates or nitrogen bases. Examples include sodium hydride, sodium methoxide, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

The reaction can be carried out under atmospheric pressure or under elevated pressure and is preferably carried out under atmospheric pressure. Work-up is carried out by customary methods.

The process (G) according to the invention is characterized in that compounds of the formulae (I-1-a) to (I-3-a) are in each case reacted with sulphonyl chlorides of the formula (IX), if appropriate in the presence of a diluent and if appropriate in the presence of an acid binder.

In the preparation process (G), approximately 1 mol of sulphonyl chloride of the formula (IX) per mole of starting material of the formula (I-1-a) to (I-3-a) is reacted at $-20$ to $150°$ C., preferably at 0 to $70°$ C.

The process (G) is preferably carried out in the presence of a diluent.

Suitable diluents are all inert polar organic solvents such as ethers, amides, ketones, carboxylic esters, nitrites, sulphones, sulphoxides or halogenated hydrocarbons such as methylene chloride.

Preference is given to using dimethyl sulphoxide, tetrahydrofuran, dimethylformamide, ethyl acetate, methylene chloride.

If, in a preferred embodiment, the enolate salt of the compounds (I-1-a) to (I-3-a) is prepared by addition of strong deprotonating agents (such as, for example, sodium hydride or potassium tert-butoxide), the addition of acid binders can be dispensed with.

If acid binders are used, then customary inorganic or organic bases are suitable, examples being sodium hydroxide, sodium carbonate, potassium carbonate, pyridine and triethylamine.

The reaction can be carried out under atmospheric pressure or under elevated pressure and is preferably carried out under atmospheric pressure. Work-up is carried out by customary methods.

The process (H) according to the invention is characterized in that compounds of the formulae (I-1-a) to (I-3-a) are in each case reacted with phosphorus compounds of the formula (X), if appropriate in the presence of a diluent and if appropriate in the presence of an acid binder.

In the preparation process (H), 1 to 2, preferably 1 to 1.3, mol of the phosphorus compound of the formula (X) are reacted per mole of the compounds (I-1-a) to (I-3-a), at temperatures between $-40°$ C. and $150°$ C., preferably between $-10$ and $110°$ C., to obtain compounds of the formulae (I-1-e) to (I-3-e).

The process (H) is preferably carried out in the presence of a diluent.

Suitable diluents are all inert, polar organic solvents such as ethers, carboxylic esters, halogenated hydrocarbons, ketones, amides, nitrites, sulphones, sulphoxides, etc.

Preference is given to using acetonitrile, dimethyl sulphoxide, tetrahydrofuran, dimethylformamide, methylene chloride.

Acid binders which are added, if appropriate, are customary inorganic or organic bases, such as hydroxides, carbonates or amines. Examples include sodium hydroxide, sodium carbonate, potassium carbonate, pyridine and triethylamine.

The reaction can be carried out under atmospheric pressure or under elevated pressure and is preferably carried out under atmospheric pressure. Work-up is carried out according to customary methods of organic chemistry. The end products are preferably purified by crystallization, chromatographic purification or by so-called "encipient distillation", i.e. removal of the volatile components under reduced pressure.

The process (I) is characterized in that compounds of the formulae (I-1-a) to (I-3-a) are in each case reacted with metal hydroxides or metal alkoxides of the formula (XI) or amines of the formula (XII), if appropriate in the presence of a diluent.

Diluents which are preferred for use in the process (I) according to the invention are ethers such as tetrahydrofuran, dioxane, diethyl ether, or else alcohols such as methanol, ethanol, isopropanol, but also water. The process (I) according to the invention is generally carried out under atmospheric pressure. The reaction temperature is generally between −20° C. and 100° C., preferably between 0° C. and 50° C.

The process (J) according to the invention is characterized in that compounds of the formulae (I-1-a) to (I-3-a) are in each case reacted with (Jα) compounds of the formula (XIII), if appropriate in the presence of a diluent and if appropriate in the presence of a catalyst, or (Jβ) with compounds of the formula (XIV), if appropriate in the presence of a diluent and if appropriate in the presence of an acid binder.

In the preparation process (Jα), approximately 1 mol of isocyanate of the formula (XI) is reacted per mole of starting material of the formulae (I-1-a) to (I-3-a) at 0 to 100° C., preferably at 20 to 50° C.

The process (Jα) is preferably carried out in the presence of a diluent.

Suitable diluents are all inert organic solvents, such as aromatic hydrocarbons, halogenated hydrocarbons, ethers, amides, nitriles, sulphones or sulphoxides.

If appropriate, catalysts may be added to accelerate the reaction. Catalysts which can be employed very advantageously are organotin compounds, such as, for example, dibutyltin dilaurate.

The process is preferably carried out under atmospheric pressure.

In the preparation process (Jβ), approximately 1 mol of carbamoyl chloride of the formula (XIV) is reacted per mole of starting material of the formulae (I-1-a) to (I-3-a) at 0 to 150° C., preferably at 20 to 70° C.

Diluents which may be added, if appropriate, are all inert polar organic solvents such as ethers, carboxylic esters, nitrites, ketones, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound (I-1-a) to (I-3-a) is prepared by addition of strong deprotonating agents (such as, for example, sodium hydride or potassium tert-butoxide), the addition of acid binders can be dispensed with.

If acid binders are employed, then customary inorganic or organic bases are suitable, examples including sodium hydroxide, sodium carbonate, potassium carbonate, triethylamine or pyridine.

The reaction can be carried out under atmospheric pressure or under elevated pressure and is preferably carried out under atmospheric pressure. Work-up is carried out by customary methods.

The active compounds are suitable for controlling animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blatella germanica, Acheta domesticus,* Gryllotalpa spp., *Locusta migratoria migratorioides, Melanoplus differentialis* and *Schistocerca gregaria.*

From the order of the Dernaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Frankliniella occidentalis, Hercinothrips femoralis, Thrips palmi* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi.* Empoasca spp., *Euscelis bilobatus, Nephotettix cincticeps, Lecanium comi, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp, *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamensis, Antho nomus* spp., Sitophilus spp., *Otiorrhynchus sulcatus, Cosmopolites sordidus, Ceuthorrhynchus assimilis,* Hypera postica, Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon soisti tialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Liriomyza spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds according to the invention have a high insecticidal and acaricidal activity.

They can be used to particularly good effect for controlling insects which are injurious to plants, such as, for example, against the larvae of the mustard beetle (*Phaedon cochleariae*), or against the larvae of the green rice leaf hopper (*Nephotettix cincticeps*) and against the caterpillars of the cabbage moth (*Plutella maculipennis*).

The active compounds according to the invention can furthermore be used as defoliants, desiccants, haulm killers and, especially, as weedkillers. By weeds, in the broadest sense, there are to be understood all plants which grow in locations where they are not wanted. Whether the substances according to the invention act as total or selective herbicides depends essentially on the amount used.

The doses of the active compounds according to the invention necessary to control weeds are between 0.001 and 10 kg/ha, preferably between 0.005 and 5 kg/ha.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotola, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with and without tree plantings. Equally, the compounds can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land and for the selective control of weeds in annual crops.

The active compounds according to the invention are particularly suitable for the selective control of monocotyledonous weeds in dicotyledonous crops, both pre-emergence and post-emergence. In cotton and sugar beet, for example, they can be employed very successfully for controlling weed grasses.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifying agents and/or dispersing agents and/or foam-forming agents.

If the extender used is water, it is also possible to use, for example, organic solvents as auxiliary solvents. Essentially, suitable liquid solvents include: aromatics, such as xylene, toluene or alkylnaphthalenes, chlorinated aromatics and chlorinated aliphatic hydrocarbons, such as chlorobenzenes, chloroethylenes of methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are:

for example ammonium salts and ground natural minerals, such as kaolins, clays, talc, chalk, quartz, attapulgite, montrnorillonite or diatomaceous earth, and ground synthetic minerals, such as highly disperse silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates and also protein hydrolysates; suitable dispersing agents are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%, and additionally preferably extenders and surfactants.

The active compound according to the invention can be present in its commercially available fonnulations and in the use forms prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

Examples of particularly advantageous mixture components are the following compounds:

Fungicides:
  2-aminobutane; 2-anilino-4-methyl-6-cyclopropyl-pyrimidine; 2',6'-dibromo-2-methyl-4'-trifluoromethoxy4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]-acetate; 2-phenylphenol (OPP), aldimorph, ampropylfos, anilazine, azaconazole,
  benalaxyl, benodanil, benomyl, binapacryl, biphenyl, bitertanol, blasticidin-S, bromuconazole, bupirimate, buthiobate,
  calcium polysulphide, captafol, captan, carbendazim, carboxin, quinomethionate, chloroneb, chloropicrin, chlorothalonil, chlozolinate, cufraneb, cymoxanil, cyproconazole, cyprofuram,
  dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon,
  edifenphos, epoxyconazole, ethirimol, etridiazole,
  fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox,
  guazatine,
  hexachlorobenzene, hexaconazole, hymexazol,
  imazalil, irnibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture,
  mancopper, mancozeb, maneb, mepanipyrim, mepronil, metalaxyl, metconazole, methasulphocarb, methfuroxam, metiram, metsulphovax, myclobutanil,
  nickel dimethyldithiocarbamate, nitrothal-isopropyl, nuarimol,
  ofurace, oxadixyl, oxamocarb, oxycarboxin,
  pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon,
  quintozene (PCNB),
  sulphur and sulphur preparations,
  tebucanozole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole,
  validamycin A, vinclozolin,
  zineb, ziram.

Bactericides:
  bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
  abamectin, AC 303 630, acephate, acrinathrin, alanycarb, aldicarb, alphamethrin, amitraz, avermectin, AZ 60541, azadirachtin, azinphos A, azinphos M, azocyclotin,
  *Bacillus thuringiensis*, bendiocarb, benfuracarb, bensultap, beta-cyluthrin, bifenthrin, BPMC, brofenprox, bromophos A, bufencarb, buprofezin, butocarboxin, butylpyridaben,
  cadusafos, carbaryl, carbofuran, carbophenothion, carbosulphane, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
  deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton,
  edifenphos, emamectin, esfenvalerate, ethiofencarb, ethion, ethofenprox,
  ethoprophos, etrimphos,
  fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb,
  HCH, heptenophos, hexaflumuron, hexythiazox,
  imidacloprid, iprobenfos, isazophos, isofenphos, isoprocarb, isoxathion, ivemectin, lambda-cyhalothrin, lufenuron,
  malathion, mecarbam, mevinphos, mesulphenphos, metaldehyde, methacrifos, methamidophos, methidathion, methiocarb, methomyl, metolcarb, milbemectin, monocrotophos, moxidectin,
  naled, NC 184, NI 25, nitenpyram,
  omethoate, oxamyl, oxydemethon M, oxydeprofos,
  parathion A, parathion M, permethrin, phenthoate, phorate, phosalone, phosmet, phosphamidon, phoxim, pirirnicarb, pirimiphos M, primiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen,
  quinalphos,
  RH 5992,
  salithion, sebufos, silafluofen, sulphotep, sulprofos,
  tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
  vamidothion, XMC, xylylcarb, YI 5301/5302, zetamethrin.

Herbicides:
  for example anilides such as, for example, diflufenican and propanil; arylcarboxylic acids such as, for example, dichloropicolinic acid, dicamba and picloram; aryloxy-alkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenz-thiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulphuron, bensulphuron-methyl, chlorimuron-ethyl, chlorsulphuron, cinosulphuron, metsulphuron-methyl, nicosulphuron, primisulphuron, pyrazosulphuron-ethyl, thifensulphuron-methyl, triasulphuron and tribenuron-methyl; thiocarbamates such as, for example, butylate, cycloate, di-allate, EPTC, esprocarb, molinate, prosulphocarb, thiobencarb and tri-allate; triazines such as, for example, atrazine, cyanazine, simazine, simetryne, terbutryne and terbutylazine; triazinones such as for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms prepared from these formulations, as a mixture with synergistic agents. Synergistic agents are compounds which increase the action of the active compounds without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound has excellent residual action on wood and clay and also a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example Argas spp., Ornithodorus spp., Otabius spp., Ixodes spp., Amblyommna spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Octodectes spp., Sarcoptes spp., Notoedres spp., Knemidocoptes spp., Cytodites spp. and Laminosioptes spp.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea-pigs, rats and mice. By controlling these arthropods, it is intended to reduce mortality and decreased performance (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluscs, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*, Xyleborus spec., Tryptodendron spec., *Apate monachus, Bostrychus capucins, Heterobostrychus brunneus*, Sinoxylon spec., *Dinoderus minutus*.

Dermapterans, such as

*Sirex juvencus, Urocerus gigas, Urocerus gigas taignus, Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as

*Lepisma saccharina.*

Industrial materials are to be understood as meaning, in the present context, non-live materials such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example: construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemnical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oilcontaining solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylene benzophenone.

Particularly suitable as a solvent or diluent is also water, if appropriate as a mixture with one or more of the above-mentioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorofluanide, tolylfluanide, 3-iodo-2-propinylbutyl carbamate, N-octylsothiazolin-3-one and 4,5-dichloro-N-octylisothiazolin-3-one.

The preparation and the use of the active compounds according to the invention can be seen from the examples below.

EXAMPLES

Example I-1-a-1

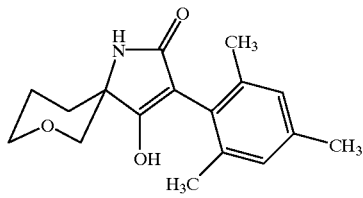

At reflux temperature, 17.3 g of the compound of Example II-1 in 160 ml of absolute toluene are added dropwise to 14.05 g (0.125 mol) of potassium tert-butoxide in 54 ml of absolute tetrahydrofuran (THF), and the mixture is stirred at this temperature for another 1.5 hours. After cooling, 160 ml of water are added, the phases are separated, the toluene phase is extracted with 80 ml of water and the combined aqueous phases are acidified with concentrated HCL at from 0 to 20° C. The product is filtered off with suction, washed, dried and then, for further purification, stirred with methyl tert-butyl(MTB)ether/N-hexane, filtered off with suction and dried. Yield: 12.1 g (77% of theory), m.p.: 200° C.

Similarly, and/or according to the general preparation procedures, the following compounds of the formula (I-1-a) are obtained:

TABLE 4

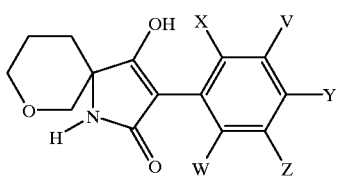

(I-1-a)

| Ex. No. | V | W | X | Y | Z | m.p.° C |
|---|---|---|---|---|---|---|
| I-1-a-2 | H | CH$_3$ | CH$_3$ | CH$_3$ | CH$_3$ | 219 |
| I-1-a-3 | H | CH$_3$ | CH$_3$ | Br | H | >220 |
| I-1-a-4 | H | H | CH$_3$ | CH$_3$ | H | 226 |
| I-1-a-5 | H | H | Cl | Cl | H | >220 |
| I-1-a-6 | H | H | CH$_3$ | CH$_3$ | CH$_3$ | 130 |
| I-1-a-7 | H | H | CH$_3$ | H | CH$_3$ | 187 |
| I-1-a-8 | H | Br | Cl | CH$_3$ | H | >220 |
| I-1-a-9 | H | H | CH$_3$ | Br | CH$_3$ | >220 |
| I-1-a-10 | H | Cl | CH$_3$ | Cl | H | >220 |
| I-1-a-11 | H | H | Br | CH$_3$ | CH$_3$ | 145 |
| I-1-a-12 | H | CH$_3$ | CH$_3$ | H | Br | 194 |
| I-1-a-13 | H | CH$_3$ | CH$_3$ | CH$_3$ | Br | |

Example (I-1-b-1)

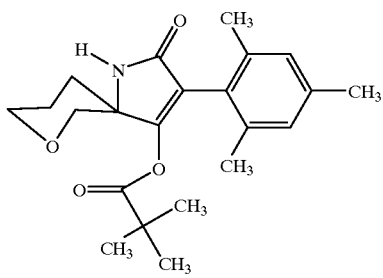

Under reflux, 2.88 g (0.010 mol) of the compound of Example (I-1-a-1) and 2.1 ml (15 nmol) of triethylamine in 50 ml of anhydrous ethyl acetate are admixed with 1.85 ml (0.15 mol) of pivaloyl chloride in 5 ml of anhydrous ethyl acetate. The mixture is stirred under reflux until the reaction has, according to thin-layer-chromatographic analysis, ended. For work-up, the reaction mixture is concentrated, taken up in methylene chloride, washed twice with 50 ml of 0.5 N aqueous sodium hydroxide solution, dried over magnesium sulphate and concentrated. The crude product is recrystallized from MTB etherlN-hexane. Yield: 2.0 g (53% of theory), m.p.: 193° C.

Similarly, and/or according to the general preparation procedures, the following compounds of the formula (I-b-1) are obtained:

TABLE 5

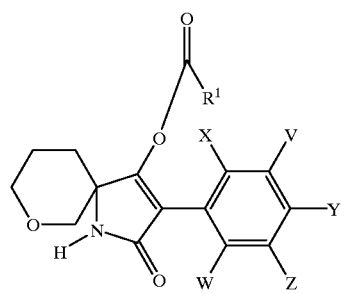

(I-1-b)

| Ex. No. | V | W | X | Y | Z | R$^1$ | m.p.° C. |
|---|---|---|---|---|---|---|---|
| I-1-b-2 | H | CH$_3$ | CH$_3$ | CH$_3$ | H | i-C$_3$H$_7$ | 163 |
| I-1-b-3 | H | CH$_3$ | CH$_3$ | CH$_3$ | CH$_3$ | i-C$_3$H$_7$ | 153 |
| I-1-b-4 | H | CH$_3$ | CH$_3$ | CH$_3$ | CH$_3$ | 2-thienyl | >220 |
| I-1-b-5 | H | CH$_3$ | CH$_3$ | Br | H | i-C$_3$H$_7$ | 190 |
| I-1-b-6 | H | CH$_3$ | CH$_3$ | Br | H | 2-thienyl | >220 |
| I-1-b-7 | H | CH$_3$ | CH$_3$ | Br | H | 4-Cl-phenyl | 209 |

TABLE 5-continued (I-1-b)

| Ex. No. | V | W | X | Y | Z | R¹ | m.p.° C. |
|---|---|---|---|---|---|---|---|
| I-1-b-8 | H | CH₃ | H | H | CH₃ | i-C₃H₇ | 178 |
| I-1-b-9 | H | CH₃ | H | CH₃ | CH₃ | i-C₃H₇ | 173 |
| I-1-b-10 | H | CH₃ | H | CH₃ | CH₃ | s-C₄H₉ | 193 |
| I-1-b-11 | H | CH₃ | H | CH₃ | H | i-C₃H₇ | 183 |
| I-1-b-12 | H | Cl | H | Cl | H | i-C₃H₇ | 108 |

Example (I-1-c-1)

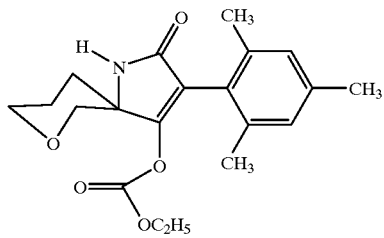

At 0–10° C., 1.0 ml (0.010 mol) of ethyl chloroformate in 5 ml of anhydrous methylene chloride are added dropwise to 2.88 g (0.010 mol) of the compound of Example (I-1-a-1) and 1.4 ml (0.010 mol) of triethylamine in 50 ml of anhydrous CH$_2$Cl$_2$, and the mixture is stirred at room temperature until the reaction has, according to thin-layer-chromatographic analysis, ended. For work-up, the mixture is washed twice with 50 ml of 0.5 N aqueous sodium hydroxide solution, dried over magnesium sulphate and concentrated. Yield: 2.8 g (77% of theory), m.p.: 157° C.

Similarly, and/or according to the general preparation procedures, the following compounds of the formula (I-1-c) are obtained:

TABLE 6

(I-1-c)

| Ex. No. | V | W | X | Y | Z | L | M | R² | m.p.° C. |
|---|---|---|---|---|---|---|---|---|---|
| I-1-c-2 | H | CH₃ | CH₃ | CH₃ | CH₃ | O | O | C₂H₅ | 163 |

TABLE 6-continued (I-1-c)

| Ex. No. | V | W | X | Y | Z | L | M | R² | m.p.° C. |
|---|---|---|---|---|---|---|---|---|---|
| I-I-c-3 | H | CH₃ | CH₃ | Br | H | O | O | C₂H₅ | 184 |
| I-l-c-4 | H | H | Cl | Cl | H | O | O | C₂H₅ | 131 |

Example II-1

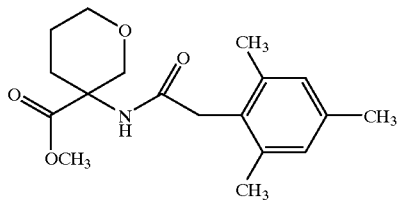

At 30–40° C., 29.1 g (0.1016 mol) of the compound of Example (XXV-1) in 310 ml of anhydrous methylene chloride are carefully added dropwise to 51.3 g (0.513 mol) of conc. sulphuric acid, and the mixture is stirred at this temperature for 2 hours. 69 ml of absolute methanol are then added dropwise in such a way that an internal temperature of approximately 40° C. results, and stirring is continued at from 40 to 70° C. for another 6 hours.

For work-up, the mixture is poured onto 0.51 kg of ice, extracted with methylene chloride, washed with aqueous sodium bicarbonate solution, dried and concentrated. The residue is recrystallized from methyl tert-butyl ether/N hexane. Yield: 17.3 g (53% of theory): m.p.: 168° C.

Similarly to Example (II-1) and according to the general preparation procedures, the following compounds of the formula (II) are prepared.

TABLE 7

(II)

| Ex. No. | V | W | X | Y | Z | R⁸ | m.p.° C. |
|---|---|---|---|---|---|---|---|
| II-2 | H | CH₃ | CH₃ | CH₃ | CH₃ | CH₃ | 78 |
| II-3 | H | CH₃ | CH₃ | Br | H | CH₃ | 110 |
| II-4 | H | H | CH₃ | CH₃ | H | CH₃ | 68 |
| II-5 | H | H | Cl | Cl | H | CH₃ | 103 |
| II-6 | H | H | CH₃ | CH₃ | CH₃ | CH₃ | 92 |

TABLE 7-continued (II)

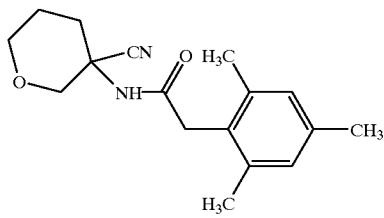

| Ex. No. | V | W | X | Y | Z | R⁸ | m.p.° C. |
|---|---|---|---|---|---|---|---|
| II-7 | H | Br | Cl | CH₃ | H | CH₃ | 114 |
| II-8 | H | Cl | CH₃ | Cl | H | CH₃ | 204 |
| II-9 | H | H | CH₃ | H | CH₃ | CH₃ | 74 |
| II-10 | H | H | CH₃ | H | H | CH₃ | 85 |
| II-11 | H | H | Br | CH₃ | CH₃ | CH₃ | 81 |
| II-12 | H | H | CH₃ | Br | CH₃ | CH₃ | 110 |
| II-13 | H | CH₃ | CH₃ | H | Br | CH₃ | 134 |
| II-14 | H | H | Cl | —O—CF₂—O— | | CH₃ | 121 |
| II-15 | H | CH₃ | CH₃ | CH₃ | Br | CH₃ | 97 |

Example XXV-1

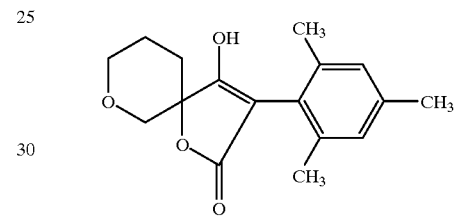

At 0–10° C., 25 g of mesityleneacetyl chloride in 30 ml of absolute THF are added dropwise to 15.8 g of 3-aminotetrahydropyran-3-carbonitrile (according to Example XXIV) and 17.6 ml of triethylamine in 250 ml of absolute THF, and the mixture is stirred until the reaction has ended. The mixture is stirred into a mixture of 500 ml of ice-water and 200 ml of 1 N HCl. The product is filtered off with suction and the residue is taken up in methylene chloride, dried and concentrated. Yield: 29.1 g (81% of theory), m.p. 153° C.

Similarly to Example (XXV-1), and/or according to the general preparation procedures, the following compounds of the formula (XXV) are prepared:

TABLE 8

(XXV)

| Ex. No. | V | W | X | Y | Z | m.p.° C. |
|---|---|---|---|---|---|---|
| XXV-2 | H | CH₃ | CH₃ | CH₃ | CH₃ | 182 |
| XXV-3 | H | CH₃ | CH₃ | Br | H | 187 |
| XXV-4 | H | H | CH₃ | CH₃ | H | 137 |
| XXV-5 | H | H | Cl | Cl | H | 162 |
| XXV-6 | H | H | CH₃ | CH₃ | CH₃ | 159 |
| XXV-7 | H | Br | Cl | CH₃ | H | 158 |
| XXV-8 | H | Cl | CH₃ | Cl | H | 141 |
| XXV-9 | H | H | CH₃ | H | CH₃ | 148 |
| XXV-10 | H | H | CH₃ | H | H | 149 |
| XXV-11 | H | CH₃ | CH₃ | H | Br | 176 |
| XXV-12 | H | H | Br | CH₃ | CH₃ | 135 |
| XXV-13 | H | H | CH₃ | Br | CH₃ | 166 |
| XXV-14 | H | H | Cl | —O—CF₂—O— | | 115 |
| XXV-15 | H | CH₃ | CH₃ | CH₃ | Br | 212 |

Example I-2-a-1

At 10° C., 18.1 g (0.057 mol) of the compound of Example III-1 in 30 ml of dry dimethylformamide (DMF) are slowly added dropwise to 9.58 g (0.085 mol) of potassium tert-butoxide in 10 ml of dry DMF, and the mixture is stirred at room temperature overnight. The DMF is distilled off and the residue is taken up in 1 l of water and slowly acidified using concentrated HCl. The product is filtered off with suction, washed with water and dried under reduced pressure at 50° C. m.p. 261° C.

Similarly to Example (I-2-a-1) and according to the general procedures, the following compounds of the formula (I-2-a) are obtained:

(I-2-a)

| Ex. No. | V | W | X | Y | Z | m.p.° C. |
|---|---|---|---|---|---|---|
| I-2-a-2 | H | CH₃ | CH₃ | Cl | H | 266–269 |
| I-2-a-3 | H | H | CH₃ | CH₃ | CH₃ | 213–214 |
| I-2-a-4 | H | CH₃ | Br | CH₃ | H | 245 |
| I-2-a-5 | H | CH₃ | CH₃ | Br | H | 270 |
| I-2-a-6 | H | CH₃ | Cl | CH₃ | H | 248–250 |
| I-2-a-7 | H | CH₃ | CH₃ | CH₃ | CH₃ | 218 |

Example I-2-b-1

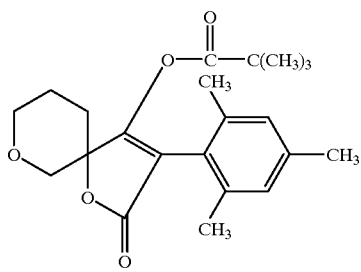

1.45 g (0.012 mol) of pivaolyl chloride are added dropwise to 2.88 g (0.01 mol) of the compound of Example I-2-a-1 and 1.2 g (0.012 mol) of triethylamine in 30 ml of anhydrous methylene chloride, and the mixture is stirred until the reaction has ended. This is followed by customary work-up. Yield: 3.47 g, m.p.: 108° C.

Similarly to Example (I-2-b-1) and according to the general procedures, the following compounds of the formula (I-2-b) are obtained:

(I-2-b)

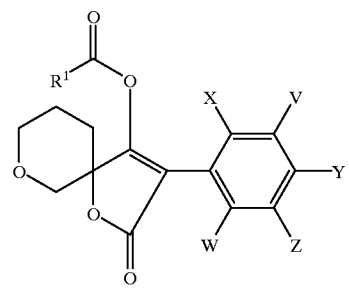

| Ex. No. | V | W | X | Y | Z | R$^1$ | m.p.° C. |
|---|---|---|---|---|---|---|---|
| I-2-b-2 | H | H | CH$_3$ | CH$_3$ | CH$_3$ | i-C$_3$H$_7$ | 106–107 |
| I-2-b-3 | H | CH$_3$ | CH$_3$ | CH$_3$ | H | i-C$_3$H$_7$ | 115 |
| I-2-b-4 | H | CH$_3$ | CH$_3$ | Cl | H | i-C$_3$H$_7$ | 109–110 |
| I-2-b-5 | H | CH$_3$ | Br | CH$_3$ | H | i-C$_3$H$_7$ | 94 |
| I-2-b-6 | H | CH$_3$ | CH$_3$ | Br | H | i-C$_3$H$_7$ | 118 |
| I-2-b-7 | H | CH$_3$ | Cl | CH$_3$ | H | i-C$_3$H$_7$ | 96–98 |
| I-2-b-8 | H | CH$_3$ | CH$_3$ | CH$_3$ | CH$_3$ | i-C$_3$H$_7$ | 115 |

Example I-2-c-1

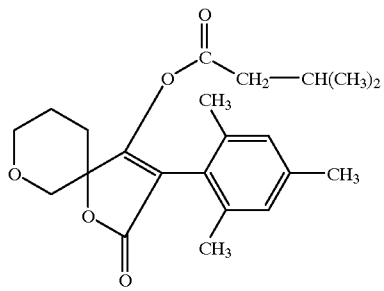

1.64 g (0.012 mol) of isobutyl chloroformate are added dropwise to 2.88 g (0.01 mol) of the compound of Example I-2-a-1 and 1.2 g (0.012 mol) of triethylamine in 30 ml of anhydrous methylene chloride, and the mixture is stirred until the reaction has ended. This is followed by customary work-up. Yield: 3.8 g, m.p.: 107° C.

Similarly to Example (I-2-c-1) and according to the general preparation procedures, the following compounds of the formula (I-2-c) are obtained:

(I-2-c)

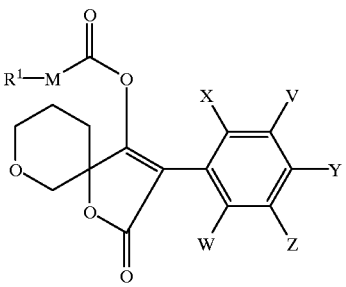

| Ex. No. | V | W | X | Y | Z | M | R$^2$ | m.p.° C. |
|---|---|---|---|---|---|---|---|---|
| I-2-c-2 | H | H | CH$_3$ | CH$_3$ | CH$_3$ | O | i-C$_4$H$_9$ | 102–103 |
| I-2-c-3 | H | CH$_3$ | CH$_3$ | CH$_3$ | H | S | i-C$_3$H$_7$ | 105–106 |
| I-2-c-4 | H | CH$_3$ | CH$_3$ | Cl | H | O | i-C$_4$H$_9$ | 143 |
| I-2-c-5 | H | CH$_3$ | Br | CH$_3$ | H | O | i-C$_4$H$_9$ | 89 |
| I-2-c-6 | H | CH$_3$ | CH$_3$ | Br | H | O | i-C$_4$H$_9$ | 138 |
| I-2-c-7 | H | CH$_3$ | Cl | CH$_3$ | H | O | i-C$_4$H$_9$ | 90–92 |
| I-2-c-8 | H | CH$_3$ | CH$_3$ | CH$_3$ | CH$_3$ | O | i-C$_4$H$_9$ | 95 |

Example (I-2-a-2)

Similarly to Example I-2-a-1, but starting with the compound of Example (III-2), the compound

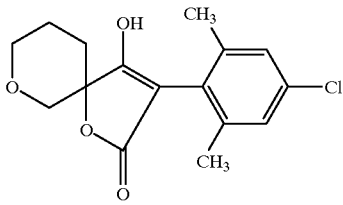

is obtained. m.p. 266–269° C.

Example (III-1)

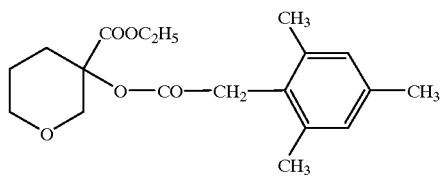

10 g (0.057 mol) of the compound of Example (XXVI) and 11.3 g of 2,4,6-trimethyl-phenyl-acetyl chloride are heated at 140° C. for 6 hours and subsequently degassed.

Yield 18.1 g of an oil, mass spectrum (MS) (m/e): 334 (M+, 36%), 160 (38%), 133 (100%).

Similarly to Example (III-1), and/or according to the general preparation procedures, the following compounds of the formula (III) are obtained:

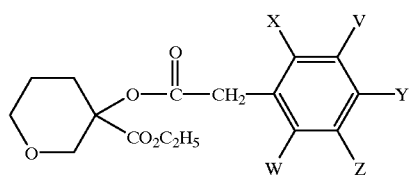

| Ex. No. | V | W | X | Y | Z | m.p.° C. |
|---|---|---|---|---|---|---|
| III-2 | H | CH$_3$ | CH$_3$ | Cl | H | oil |
| III-3 | H | H | CH$_3$ | CH$_3$ | CH$_3$ | oil |
| III-4 | H | CH$_3$ | Br | CH$_3$ | H | oil |
| III-5 | H | CH$_3$ | CH$_3$ | Br | H | oil |
| III-6 | H | CH$_3$ | Cl | CH$_3$ | H | oil |
| III-7 | H | CH$_3$ | CH$_3$ | CH$_3$ | CH$_3$ | oil |

Example XXIV

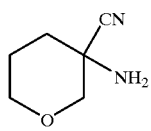

(XXIV)

At room temperature, 116.8 g (1.17 mol) of 3-oxa-cyclohexa-1-one (see Bull. Soc. Chim. Fr. (1970), (10), 3521–3) are added dropwise to a mixture of 222.4 g (3.27 mol) of 25% strength ammonia solution, 75 g (1.4 mol) of ammonium chloride, 68.7 g (1.4 mol) of sodium cyanide and 210 ml of water, and the mixture is stirred at 45° C. overnight. Extraction with methylene chloride gives 95.2 g (64% of theory) of the compound depicted above which was used without any further purification for preparing the compounds of the formula XXV.

Example (XXVI)

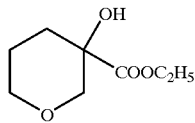

At from 0 to −20° C., the mixture of 89.3 g (0.7 mol) of the compound of Example (XXVIa) in 420 ml of ethanol is saturated with HCl. The mixture is stirred at 0° C. for another hour and then allowed to warm to room temperature over a period of about 3 hours.

Excess HCl is removed under reduced pressure and the mixture is then concentrated. The residue is admixed with 400 ml of cold water and stirred for 1 hour. This mixture is extracted twice with methylene chloride, and the extract is dried and concentrated.

Yield 90 g, bp$_{0.06}$66° C.

Example (XXVIa)

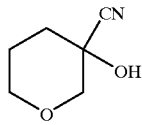

At room temperature, 24.3 g (0.9 mol) of hydrocyanic acid are added dropwise to 85.0 g (0.85 mol) of 3-oxa-cyclohexa-1-one (Bull. Soc. Chim. Fr. (1970) (10), 3521–3) and 0.72 ml of triethylamine, and the mixture is stirred at room temperature for another 1.5 hours. The mixture is stabilized with 0.12 ml of o-phosphoric acid and degassed under water pump vacuum.

Yield: 102 g (94% of theory).

USE EXAMPLES

Example A

Myzus-Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested by peach aphids (*Myzus persicae*) are treated by being dipped into the preparation of active compound of the desired concentration.

After the desired period of time, the kill in % is determined. 100% means that all aphids have been killed; 0% means that none of the aphids have been killed.

In this test, for example the compounds of Preparation Examples (I-1-a-2), (I-1-a-3), (I-1-b-2) and (I-1-c-1) effected at an exemplary concentration of active compound of 0.1%, a kill of 100% after 6 days.

Example B

Nephotettix-Test

Solvent: 20 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of active compound of the desired concentration and are populated with the green rice leaf hoppers (*Nephotettix cincticeps*) while the seedlings are still moist.

After the desired period of time, the kill in % is determined. 100% means that all leaf hoppers have been killed; 0% means that none of the leaf hoppers have been killed.

In this test, for example the compounds of Preparation Examples (I-1-a-1), (I-1-a-2), (I-1-a-3), (I-1-b-1), (I-1-b-2), (I-1-b-3), (I-1-b4), (I-1-b-5) and (I-1-c-3) effected, at an exemplary concentration of active compound of 0.1%, a kill of 100% after 6 days.

Example C

Phaedon larvae test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example the compounds of Preparation Examples (I-1-a-1), (I-1-a-2), (I-1-a-3), (I-1-b-1), (I-1-b-2), (I-1-b-3), (I-1-b-4), (I-1-b-5) and (I-1-c-1) effected, at an exemplary concentration of active compound of 0.1%, a kill of 100% after 7 days.

Example D

*Spodoptera frugiperda* Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with caterpillars of the owlet moth *Spodoptera frugiperda*) while the leaves are still moist.

After the desired period of time, the kill in % is determined. 100% means that all caterpillars have been killed; 0% means that none of the caterpillars have been killed.

In this test, for example the compounds of Preparation Examples (I-1-b4) and (I-1-c-1) effected, at an exemplary concentration of active compound of 0.1%, a kill of 100% after 7 days.

Example E

Tetranychus test (OP-resistent/dip treatment)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested by all stages of the greenhouse red spider mite *Tetranychus urticae* are dipped into a preparation of active compound of the desired concentration.

After the desired period of time, the kill in % is determined. 100% means that all spider mites have been killed; 0% means that none of the spider mites have been killed.

In this test, for example the compounds of Preparation Examples (I-1-a-1), (I-1-b-1), (I-1-b-2) und (I-1-c-1) effected, at an exemplary concentration of active compound of 0.1%, a kill of 100% after 13 days.

What is claimed is:
1. Compounds of the formula (I),

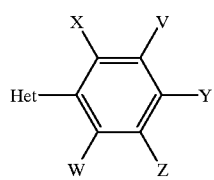

(I)

wherein
V represents hydrogen, halogen, alkyl or alkoxy,
W represents hydrogen, cyano, nitro, halogen, alkyl, alkenyl, alkynyl, alkoxy, halogenoalkyl, halogenoalkoxy, or represents unsubstituted or substituted phenyl, phenoxy, phenylthio, phenylalkoxy or phenylalkylthio,
X represents halogen, alkyl, alkenyl, alkynyl, alkoxy, halogenoalkyl, halogenoalkoxy, cyano, nitro, or represents unsubstituted or substituted phenyl, phenoxy, phenylthio, phenylalkyloxy or phenylalkylthio,
Y represents hydrogen, halogen, alkyl, alkoxy, halogenoalkyl, halogenoalkoxy, cyano or nitro,
Z represents hydrogen, halogen, alkyl, alkoxy, halogenoalkyl, halogenoalkoxy, hydroxyl, cyano, nitro or represents unsubstituted or substituted phenoxy, phenylthio, 5- or 6-membered hetaryloxy, 5- or 6-membered hetarylthio, phenylalkyloxy or phenylalkylthio, or
Y and Z together with the linking carbon atoms represent an unsubstituted or substituted cycle which is optionally interrupted by one or more heteroatoms, or
W and Z together with the linking carbon atoms represent an unsubstituted or substituted cycle which is optionally interrupted by one or more heteroatoms,
Het represents the group

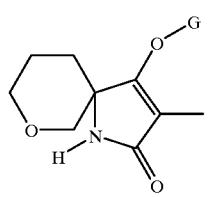

(1)

wherein
G represents hydrogen (a) or represents one of the groups (b)

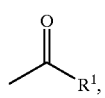

(c)

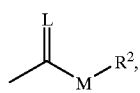

(d)

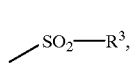

(e)

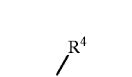

E, or (f)

(g)

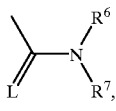

wherein
E represents a metal ion equivalent or an ammonium ion,
L represents oxygen or sulphur,
M represents oxygen or sulphur,
$R^1$ represents unsubstituted or halogen- or cyano-substituted alkyl, alkenyl, alkoxyalkyl, alkylthioalkyl, or polyalkoxyalkyl or represents unsubstituted or halogen-, alkyl- or alkoxy-substituted cycloalkyl or heterocyclyl or represents unsubstituted or substituted phenyl, phenylalkyl, hetaryl, phenoxyalkyl or hetaryloxyalkyl, $R^2$ represents unsubstituted or halogen- or cyano-substituted alkyl, alkenyl, alkoxyalkyl or polyalkoxyalkyl or represents unsubstituted or substituted cycloalkyl, phenyl or benzyl, $R^3$, $R^4$ and $R^5$ independently of one another each represent unsubstituted or halogen-substituted alkyl, alkoxy, alkylamino, dialkylamino, alkylthio, alkenylthio or cycloalkylthio or represent unsubstituted or substituted phenyl, benzyl, phenoxy or phenylthio, $R^6$ and $R^7$ independently of one another each represent hydrogen, or unsubstituted or halogen- or cyano-substituted alkyl, cycloalkyl, alkenyl, alkoxy, alkoxyalkyl, or represent unsubstituted or substituted phenyl or benzyl, or together with the linking N atom form an optionally oxygen- or sulphur-containing and optionally substituted cycle.

2. Compounds of the formula (I) according to claim 1, wherein

V represents hydrogen, halogen, $C_1$–$C_6$-alkyl or $C_1$–$C_6$-alkoxy,

W represents hydrogen, nitro, cyano, halogen, $C_1$–$C_6$-alkyl, $C_2$–$C_6$-alkenyl, $C_2$–$C_6$-alkynyl, $C_1$–$C_6$-alkoxy, $C_1$–$C_4$-halogenoalkyl, $C_1$–$C_4$-halogenoalkoxy or represents unsubstituted or halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, phenyl-$C_1$–$C_4$-alkoxy or phenyl-$C_1$–$C_4$-alkylthio, X represents halogen, $C_1$–$C_6$-alkyl, $C_2$–$C_6$-alkenyl, $C_2$–$C_6$-alkynyl, $C_1$–$C_6$-alkoxy, $C_1$–$C_4$-halogenoalkyl, $C_1$–$C_4$-halogenoalkoxy, cyano, nitro or represents unsubstituted or halogen-, $C_1$–$C_6$-alkyl, $C_1$–$C_6$-alkoxy, $C_1$–$C_4$-halogenoalkyl, $C_1$–$C_4$-halogenoalkoxy, nitro- or cyano-substituted phenyl, phenoxy, phenylthio, phenyl-$C_1$–$C_4$-alkoxy or phenyl-$C_1$–$C_4$-alkylthio, Y represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, Z represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, hydroxyl, cyano, nitro or represents unsubstituted or halogen-, $C_1$–$C_4$-alkyl-, $C_1$–$C_4$-alkoxy-, $C_1$–$C_4$-halogenoalkyl-, $C_1$–$C_4$-halogenoalkoxy-, nitro- or cyano-substituted phenoxy, phenylthio, thiazolyloxy, pyridinyloxy, pyrimidyloxy, pyrazolyloxy, phenyl-$C_1$–$C_4$-alkyloxy or phenyl-$C_1$–$C_4$-alkylthio or Y and Z together with the linking carbon atoms represent unsubstituted or halogen-, $C_1$–$C_6$-alkyl-, $C_1$–$C_6$-alkoxy- or $C_1$–$C_4$-halogenoalkyl-substituted $C_3$–$C_5$-alkanediyl or $C_3$–$C_5$-alkenediyl in which optionally one to three members may be replaced independently of one another by oxygen, sulphur, nitrogen or a carbonyl group, or W and Z together with the linking carbon atoms represent unsubstituted or halogen-, $C_1$–$C_6$-alkyl-, $C_1$–$C_5$-alkoxy- or $C_1$–$C_4$-halogenoalkyl-substituted $C_3$–$C_5$-alkanediyl or $C_3$–$C_5$-alkenediyl, wherein one to three members may be replaced independently of one another by oxygen, sulphur, nitrogen or a carbonyl group, $R^1$ represents unsubstituted or halogen- or cyano-substituted $C_1$–$C_{20}$-alkyl, $C_2$–$C_2$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl or represents unsubstituted or halogen-, $C_1$–$C_6$-alkyl- or $C_1$–$C_6$-alkoxy substituted $C_3$–$C_8$-cycloalkyl, wherein optionally one or two not directly adjacent methylene groups are replaced by oxygen and/or sulphur, or represents unsubstituted or halogen-, cyano-, nitro-, $C_1$–$C_6$-alkyl-, $C_1$–$C_6$alkoxy-, $C_1$–$C_6$-halogenoalkyl-, $_1$–$C_6$-halogenoalkoxy-, $C_1$–$C_6$-alkylthio- or $C_1$–$C_6$-alkylsulfonyl-substituted phenyl, or represents unsubstituted or halogen-, nitro-, cyano-, $C_1$–$C_6$-alkyl-, $C_1$–$C_6$alkoxy-, $C_1$–$C_6$-halogenoalkyl- or $C_1$–$C_6$-halogenoalkoxy-substituted phenyl-$C_1$–$C_6$-alkyl, or represents unsubstituted or halogen- or $C_1$–$C_6$-alkyl-substituted 5- or 6-membered hetaryl having one or two heteroatoms from the group consisting of oxygen, sulphur and nitrogen, or represents unsubstituted or halogen- or $C_1$–$C_6$-alkyl-substituted phenoxy $C_1$–$C_8$-alkyl or represents unsubstituted or halogen-, amino- or $C_1$–$C_6$-alkyl-substituted 5-or 6-membered hetaryloxy-$C_1$–$C_6$-alkyl having one or two heteroatoms from the group consisting of oxygen, sulphur and nitrogen, $R^2$ represents unsubstituted or halogen- or cyano-substituted $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, or represents unsubstituted or halogen-, $C_1$–$C_6$-alkyl- or $C_1$–$C_6$-alkoxy-substituted $C_3$–$C_8$-cycloalkyl or represents unsubstituted or halogen-, cyano-, nitro-, $C_1$–$C_6$alkyl-, $C_1$–$C_6$-alkoxy-, $C_1$–$C_6$-halogenoalkyl- or $C_1$–$C_6$–halogenoalkoxy-substituted, phenyl or benzyl, $R^3$ represents unsubstituted or halogen-substituted $C_1$–$C_8$-alkyl or represents unsubstituted or halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl, $R^4$ and $R^5$ independently of one another each represent unsubstituted or halogen-substituted $C_1$–$C_8$-alkyl, $C_1$–$C_8$-alkoxy, $C_1$–$C_8$-alkylamino, di-($C_1$–$C_8$-alkyl) amino, $C_1$–$C_8$-alkylthio or $C_3$–$C_8$alkenylthio or represent unsubstituted or halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, phenoxy or phenylthio, and $R^6$ and $R^7$ independently of one another each represent hydrogen, represent unsubstituted or halogen- or cyano-substituted $C_1$–$C_8$-alkyl, $C_3$–$C_8$-cycloalkyl, $C_1$–$C_8$-alkoxy, $C_1$–$C_8$-alkenyl or $C_1$–$C_8$-alkoxy-$C_2$–$C_8$-alkyl, represent unsubstituted or halogen-, $C_1$–$C_8$-alkyl-, $C_1$–$C_8$-halogenoalkyl- or $C_1$–$C_8$-alkoxy-substituted phenyl or benzyl or together represent an unsubstituted or $C_1$–$C_6$-alkyl-substituted $C_3$–$C_6$-alkylene radical, wherein optionally one methylene group is replaced by oxygen or sulphur.

3. Compounds of the formula (I) according to claim 1, wherein

V represents hydrogen, fluorine, chlorine, bromine, $C_1$–$C_4$-alkyl or $C_1$–$C_4$-alkoxy, W represents hydrogen, nitro, cyano, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy or represents unsubstituted or fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenyl, phenoxy or benzyloxy, X represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano, nitro or represents unsubstituted or fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenyl, phenoxy or benzyloxy, Y represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, Z represents hydrogen, fluorine, chlorine, bromine, $C_1$–$C_4$-alkyl-, $C_1$–$C_4$-alkoxy-, $C_1$–$C_2$-halogenoalkyl, $C_1$–$C_2$-halogenoalkoxy, hydroxyl, cyano, nitro or represents unsubstituted or fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenoxy or benzyloxy or Y and Z together with the linking carbon atoms represent unsubstituted or fluorine-, chlorine-, bromine-, $C_1$–$C_4$-alkyl-, $C_1$–$C_4$-alkoxy- or $C_1$–$C_2$-halogenoalkyl-substituted $C_3$–$C_4$-alkanediyl or $C_3$–$C_4$-alkenediyl, wherein optionally one or two not directly adjacent members may be replaced independently of one another by oxygen, sulphur or nitrogen, or W and Z together with the linking carbon atoms represent unsubstituted or fluorine-, chlorine-, bromine-, $C_1$–$C_4$-alkyl-, $C_1$–$C_4$-alkoxy- or $C_1$–$C_2$-halogenoalkyl-substituted $C_3$–$C_4$-alkanediyl or $C_3$–$C_4$-alkenediyl, wherein one or two not directly adjacent members may be replaced independently of one another by oxygen, sulphur or nitrogen, $R^1$ represents unsubstituted or fluorine- or chlorine-substituted $C_1$–$C_{16}$-alkyl, $C_2$–$C_6$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl or represents unsubstituted or fluorine-, chlorine-, $C_1$–$C_5$-alkyl- or or $C_1$–$C_5$-alkoxy-substituted $C_3$–$C_7$-cycloalkyl, wherein optionally one or two not directly adjacent methylene groups are replaced by oxygen and/or sulphur, or represents unsubstituted or fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl substituted phenyl, or represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, or represents unsubstituted or fluorine-, chlorine-, bromine- or $C_1$–$C_4$-alkyl-substituted pyrazolyl, thiazolyl, pyridyl, pyrimidyl, furanyl or thienyl, or represents unsubstituted or fluorine-, chlorine-, bromine-, or $C_1$–$C_4$-alkyl-substituted phenoxy-$C_1$–$C_5$-alkyl or represents unsubstituted or fluorine-, chlorine-, bromine- amino- or $C_1$–$C_4$-alkyl-substituted pyridyloxy-$C_1$–$C_5$-alkyl, pyrimidyloxy-$C_1$–$C_5$-alkyl or thiazolyloxy-$C_1$–$C_5$-alkyl, $R^2$ represents unsubstituted or fluorine- or chlorine-substituted $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, represents unsubstituted or fluorine-, chlorine-, $C_1$–$C_4$-alkyl- or $C_1$–$C_4$-alkoxy-substituted $C_3$–$C_7$-cycloalkyl or represents unsubstituted or fluorine, chlorine, bromine-, cyano, nitro, $C_1$–$C_4$-alkyl-, $C_1$–$C_3$-alkoxy-, $C_1$–$C_3$-halogenoalkyl- or $C_1$–$C_3$-halogenoalkoxy-substituted phenyl or benzyl, $R^3$ represents unsubstituted or fluorine- or chlorine-substituted $C_1$–$C_6$-alkyl or represents unsubstituted or fluorine-, chlorine-, bromine-, $C_1$–$C_4$-alkyl-, $C_1$–$C_4$-alkoxy, $C_1$–$C_2$-halogenoalkoxy-, $C_1$–$C_2$-halogenoalkyl-, cyano- or nitro-substituted phenyl or benzyl, $R^4$ and $R^5$ independently of one another each represent unsubstituted or fluorine- or chlorine-substituted $C_1$–$C_6$-alkyl-, $C_1$–$C4$-alkoxy-, $C_1$–$C_6$-alkylamino-, di-($C_1$–$C_6$-alkyl)amino, $C_1$–$C_6$-alkylthio or $C_3$–$C_4$-alkenylthio or represent unsubstituted or fluorine-, chlorine-, bromine-, nitro-, cyano-, $C_1$–$C_3$-alkoxy-, $C_1$–$C_3$-halogenoalkoxy-, $C_1$–$C_3$-alkylthio-, $C_1$–$C_3$-halogenoalkylthio-, $C_1$–$C_3$-alkyl or $C_1$–$C_3$-halogenoalkyl-substituted phenyl, phenoxy or phenylthio, and $R^6$ and $R^7$ independently of one another each represent hydrogen, represent unsubstituted or fluorine- or chlorine-substituted $C_1$–$C_6$-alkyl, $C_3C_6$-cycloalkyl, $C_1$–$C_6$-alkoxy, $C_3$–$C_6$-alkenyl or $C_1$–$C_6$-alkoxy-$C_2$–$C_6$-alkyl, represent unsubstituted or fluorine-, chlorine-, bromine-, $C_1$–$C_5$-halogenoalkyl-, $C_1$–$C_5$-alkyl- or $C_1$–$C_5$-alkoxy substituted phenyl or benzyl, or together represent an unsubstituted or $C_1$–$C_4$-alkyl-substituted $C_3$–$C_6$-alkylene radical, wherein optionally one methylene group is replaced by oxygen or sulphur.

4. Compounds of the formula (I) according to claim 1, wherein

V represents hydrogen, fluorine, chlorine, bromine, methyl, ethyl, propyl, iso-propyl, tert-butyl, methoxy, ethoxy, propoxy or iso-propoxy, W represents hydrogen, nitro, cyano, fluorine, chlorine, bromine, methyl, ethyl, propyl, n-butyl, iso-propyl, iso-butyl, methoxy, ethoxy, propoxy, iso-propoxy, trifluoromethyl, difluoromethoxy, trifluoromethoxy, phenyl or benzyloxy, X represents fluorine, chlorine, bromine, methyl, ethyl, propyl, butyl, iso-butyl, iso-propyl, methoxy, ethoxy, propoxy, iso-propoxy, trifluoromethyl, trifluoromethoxy, difluoromethoxy, cyano, nitro, phenyl or benzyloxy, Y represents hydrogen, fluorine, chlorine, bromine, methyl, ethyl, propyl, iso-propyl, n-butyl, iso-butyl, tert-butyl, methoxy, ethoxy, propoxy, iso-propoxy, trifluoromethyl, trifluoromethoxy, difluoromethoxy, cyano or nitro, Z represents hydrogen, fluorine, chlorine, bromine, methyl, ethyl, propyl, butyl, iso-butyl, iso-propyl, tert-butyl, methoxy, ethoxy, propoxy, iso-propoxy, trifluoromethyl, trifluoromethoxy, difluoromethoxy, cyano or nitro or Y and Z together with the linking carbon atoms represent unsubstituted or fluorine-, chlorine-, methyl-, ethylpropyl-, iso-propyl-, methoxy-, ethoxy-, propoxy-, iso-propoxy- or trifluoromethyl-substituted $C_3$–$C_4$-alkanediyl, wherein optionally two not directly adjacent members are replaced by oxygen or W and Z together with the linking carbon atoms represent unsubstituted or fluorine-, chlorine-, methyl-, ethyl-, propyl-, iso-propyl-, methoxy-, ethoxy-, propoxy-, iso-propoxy- or trifluoromethyl-substituted $C_3$–$C_4$alkanediyl, wherein optionally two not directly adjacent members are replaced by oxygen, $R^1$ represents unsubstituted or chlorine- or fluorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl or represents unsubstituted or fluorine-, chlorine-, methyl-, ethyl-, n-propyl-, i-propyl-, n-butyl-, i-butyl-, tert-butyl, methoxy-, ethoxy-, n-propoxy- or iso-propoxy-substituted $C_3$–$C_6$-cycloalkyl, wherein optionally one or two not directly adjacent methylene groups are replaced by oxygen and/or sulphur, or represents unsubstituted or fluorine-, chlorine-, bromine-, cyano-, nitro-, methyl-, ethyl-, n-propyl-, i-propyl-, methoxy-, ethoxy-, trifluoromethyl-, trifluoromethoxy-, methylthio-, ethylthio-, methylsulphonyl- or ethylsulphonyl-substituted phenyl, or represents unsubstituted or fluorine-, chlorine-, bromine-, methyl-, ethyl-, n-propyl-, i-propyl-, methoxy-, ethoxy-, trifluoromethyl- or trifluoromethoxy-substituted benzyl, or represents substituted or fluorine-, chlorine-, bromine-, methyl- or ethyl-substituted furanyl, thienyl or pyridyl, or represents unsubstituted or fluorine-, chlorine-, methyl- or ethyl-substituted phenoxy-$C_1$–$C_4$-alkyl or represents unsubstituted or fluorine-, chlorine-, amino-, methyl- or ethyl-substituted pyridyloxy-$C_1$–$C_4$-alkyl, pyrimidyloxy-$C_1$–$C_4$-alkyl or thiazolyloxy-$C_1$–$C_4$-alkyl, $R^2$ represents unsubstituted or fluorine- or chlorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, or represents unsubstituted or fluorine-, chlorine-, methyl-, ethyl-, n-propyl, iso-propyl- or methoxy-substituted $C_3$–$C_6$-cycloalkyl, or represents unsubstituted or fluorine-, chlorine-, cyano-, nitro-, methyl-, ethyl-, n-propyl-, i-propyl-, methoxy-, ethoxy-, trifluoromethyl- or trifluoromethoxy-substituted phenyl or benzyl, $R^3$ represents unsubstituted or fluorine- or chlorine-substituted methyl, ethyl, propyl, iso-propyl, n-butyl, tert-butyl, or represents unsubstituted or fluorine-, chlorine-, bromine-, methyl-, ethyl-, iso-propyl-, tert-butyl-, methoxy-, ethoxy-, iso-propoxy-, trifluoromethyl-, trifluoromethoxy-, cyano- or nitro-substituted phenyl or benzyl, $R^4$ and $R^5$ independently of one another each represent unsubstituted or fluorine- or chlorine-substituted $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio or represent unsubstituted or fluorine-, chlorine-, bromine-, nitro-, cyano-, methyl-, methoxy-, trifluoromethyl- or trifluoromethoxy-substituted phenyl, phenoxy or phenylthio, and $R^6$ and $R^7$ independently of one another represent hydrogen, represent unsubstituted or fluorine- or chlorine-substituted $C_1$–$C_4$-alkyl, $C_3$–$C_6$cycloalkyl, $C_1$–$C_4$-alkoxy, $C_3$–$C_4$-alkenyl or $C_1$–$C_4$-alkoxy-$C_2$–$C_4$-alkyl, represent unsubstituted or fluorine-, chlorine-, bromine-, methyl-, methoxy- or trifluoromethyl-substituted phenyl or benzyl, or together represent an unsubstituted or methyl- or ethyl-substituted $C_5$–$C_6$-alkylene radical, wherein optionally one methylene group is replaced by oxygen or sulphur.

5. A pesticidal or herbicidal composition comprising compounds of the formula (I) according to claim 1 and an acceptable diluent.

6. A method for controlling pests and weeds, comprising the step of applying at least one compound of the formula (I) according to claim 1 on pests, weeds, pest habitat, and/or weed habitat.

7. A process for preparing compounds of the formula (I) according to claim 1, wherein compounds of the formula (I-1-a)

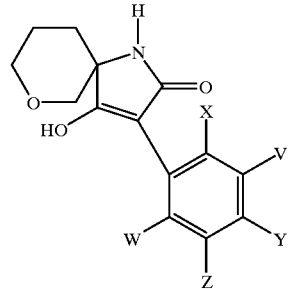

(I-1-a)

wherein V, W, X, Y and Z are each as defined in claim 1 are obtained when compounds of the formula (II)

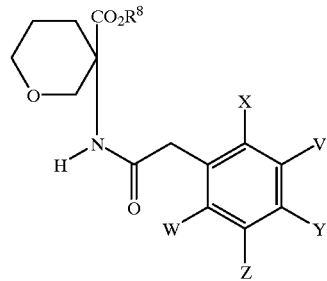

(II)

wherein V, W, X, Y and Z are each as defined above, and $R^8$ represents alkyl, are intramolecularly condensed in the presence of a diluent and in the presence of a base.

8. A process for preparing pesticides and herbicides, comprising the step of mixing compounds of the formula (I) according to claim 1, with an ingredient selected from the groug consisting of extenders, surfactants and mixtures thereof.

* * * * *